US010809210B2

(12) United States Patent
Horiba et al.

(10) Patent No.: US 10,809,210 B2
(45) Date of Patent: Oct. 20, 2020

(54) X-RAY PHASE IMAGING APPARATUS

(71) Applicant: Shimadzu Corporation, Kyoto (JP)

(72) Inventors: Akira Horiba, Kyoto (JP); Taro Shirai, Kyoto (JP); Takahiro Doki, Kyoto (JP); Satoshi Sano, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 22 days.

(21) Appl. No.: 16/463,305

(22) PCT Filed: Sep. 6, 2017

(86) PCT No.: PCT/JP2017/032073
§ 371 (c)(1),
(2) Date: May 22, 2019

(87) PCT Pub. No.: WO2018/096759
PCT Pub. Date: May 31, 2018

(65) Prior Publication Data
US 2019/0293577 A1    Sep. 26, 2019

(30) Foreign Application Priority Data
Nov. 22, 2016 (JP) ................................. 2016-226577

(51) Int. Cl.
*G01N 23/20* (2018.01)
*G01N 23/20025* (2018.01)
*A61B 6/00* (2006.01)

(52) U.S. Cl.
CPC ......... *G01N 23/20025* (2013.01); *A61B 6/00* (2013.01); *G01N 23/20* (2013.01); *G01N 23/20075* (2013.01); *G01N 2223/3303* (2013.01); *G01N 2223/3307* (2013.01); *G01N 2223/618* (2013.01)

(58) Field of Classification Search
CPC ............. G01N 23/20; G01N 23/20025; G01N 23/20075; G01N 23/041; G01N 23/06; G01N 23/083; G01N 23/04; G01N 2223/3303; G01N 2223/3307; G01N 2223/618; A61B 6/4035; A61B 6/405; A61B 6/44; A61B 6/484; A61B 6/54;
(Continued)

(56) References Cited

U.S. PATENT DOCUMENTS 9,717,470 B2    8/2017  Martens et al.
10,732,302 B2*  8/2020  Sano ...................... A61B 6/484

OTHER PUBLICATIONS

Written Opinion by the International Search Authority for PCT application No. PCT/JP2017/032073, dated Nov. 28, 2017, submitted with a machine translation.
(Continued)

*Primary Examiner* — Jurie Yun
(74) *Attorney, Agent, or Firm* — Muir Patent Law, PLLC

(57) ABSTRACT

This X-ray phase imaging apparatus (100) includes a controller (5) that generates a dark field image (Iv) with respect to each of a plurality of relative positions between a subject (S) and an imaging grating (G1) changed by an adjustment mechanism (3) to acquire a contrast of a region of interest (ROI) in the dark field image (Iv), and controls the adjustment mechanism (3) to adjust a relative position between the subject (S) and the imaging grating (G1) based on the acquired contrast.

9 Claims, 13 Drawing Sheets

(EMBODIMENT)

(58) Field of Classification Search
CPC ....... A61B 6/542; A61B 6/4291; A61B 6/483; A61B 6/588
See application file for complete search history.

(56) References Cited

OTHER PUBLICATIONS

International Search Report for PCT application No. PCT/JP2017/032073, dated Nov. 28, 2017.

\* cited by examiner (EMBODIMENT)

FIG.11 DARK FIELD IMAGE CONTRAST ADJUSTMENT PROCESSING (MODIFIED EXAMPLE)

45-DEGREE DIRECTION 135-DEGREE DIRECTION

X-RAY PHASE IMAGING APPARATUS

TECHNICAL FIELD

The present invention relates to an X-ray phase imaging apparatus, and more particularly, it relates to an X-ray phase imaging apparatus that moves a relative position between a grating and a subject.

BACKGROUND ART

Conventionally, an X-ray phase imaging apparatus that moves a relative position between a grating and a subject is known. Such an X-ray phase imaging apparatus is disclosed in Japanese Translation of PCT International Application Publication No. 2015-529510, for example.

Japanese Translation of PCT International Application Publication No. 2015-529510 discloses an X-ray imaging system apparatus (X-ray phase imaging apparatus) for differential phase contrast imaging including an X-ray source, an X-ray detector, a grating arrangement, a phase differential arrangement, and a processing unit (controller). In this X-ray imaging system apparatus, the grating arrangement includes a phase grating (imaging grating) disposed between the X-ray source and the detector, a source grating (light source grating) disposed between the phase grating and the X-ray source, and an analyser grating (absorption grating) disposed between the phase grating and the detector. The phase differential arrangement includes a grating arrangement and a moving arrangement (adjustment mechanism) for a relative movement between an object (subject) under examination and at least one of the gratings. The X-ray imaging system apparatus translates the source grating in order to produce a predetermined moire pattern (an image as a base of a phase differential image representing changes in the phases of X-rays) caused by the grating. In addition, the X-ray imaging system apparatus performs relative movement between the phase differential arrangement (a member related to optical paths of X-rays imaged in the apparatus) and the object (subject) under examination.

Furthermore, conventionally, a method for moving a phase grating (imaging grating) in a direction substantially perpendicular to X-rays radiated to the phase grating and substantially perpendicular to a direction in which grating portions of the phase grating extend in the case in which there is an object (subject) under examination on paths of X-rays incident on the grating and in the case in which there is not the object on the paths of the X-rays incident on the grating, capturing a plurality of grating images (X-ray images) generated by the phase grating with respect to each of a plurality of different positions of the phase grating, and performing a comparison is known. In this method, the plurality of grating images (X-ray images) are compared such that a dark field image representing a change in X-ray sharpness due to X-ray scattering caused by the presence or absence of the subject is acquired.

PRIOR ART

Patent Document

Patent Document 1: Japanese Translation of PCT International Application Publication No. 2015-529510

SUMMARY OF THE INVENTION

Problems to be Solved by the Invention

In the X-ray imaging system apparatus (X-ray phase imaging apparatus) for differential phase contrast imaging disclosed in Japanese Translation of PCT International Application Publication No. 2015-529510, a relative position between the object (subject) and each grating or a relative position between the subject and the phase differential arrangement (the member related to the optical paths of the X-rays imaged in the apparatus) is moved such that a predetermined moire pattern appears properly. However, even if the moire pattern appears properly as the whole X-ray image, a portion in which information about the X-ray scattering is properly detected and a portion in which the information is hardly detected are generated in the dark field image, depending on a direction in which each grating portion included in each grating extends. Specifically, the X-ray scattering is more likely to be captured in a direction perpendicular to the direction in which the grating portion extends (that is, the contrast is increased), but the X-ray scattering is less likely to be captured in a direction along the direction in which the grating portion extends (the contrast is decreased). Therefore, even when the adjustment can be made such that the moire pattern appears properly, there is a problem that the contrast is not always sufficiently obtained in a region of interest of the subject in the dark field image.

The present invention has been proposed in order to solve the aforementioned problems, and an object of the present invention is to provide an X phase imaging apparatus capable of sufficiently obtaining the contrast in a region of interest of a subject in a dark field image.

Means for Solving the Problems

In order to attain the aforementioned object, an X-ray phase imaging apparatus according to an aspect of the present invention includes an X-ray source that radiates X-rays to a subject, an imaging grating that generates a grating image by transmitting the X-rays radiated to the subject from the X-ray source, a detector that detects the X-rays that have been transmitted through the imaging grating, an adjustment mechanism that changes and adjusts a relative position between the subject and the imaging grating, and a controller that generates a dark field image representing a change in X-ray sharpness between a case in which the subject is present and a case in which the subject is not present based on signals of the X-rays detected by the detector with respect to each of a plurality of relative positions between the subject and the imaging grating changed by the adjustment mechanism to acquire a contrast of a region of interest in the dark field image, and controls the adjustment mechanism to adjust the relative position between the subject and the imaging grating based on the acquired contrast.

In the X-ray phase imaging apparatus according to this aspect of the present invention, as described above, the dark field image representing the change in X-ray sharpness between the case in which the subject is present and the case in which the subject is not present is generated based on the signals of the X-rays detected by the detector with respect to each of the plurality of relative positions between the subject and the imaging grating changed by the adjustment mechanism to acquire the contrast of the region of interest in the dark field image, and the relative position between the subject and the imaging grating is adjusted based on the acquired contrast. Accordingly, the relative position between the subject and the imaging grating is adjusted based on the contrast of the subject in the dark field image such that it is possible to sufficiently obtain the contrast in the region of interest of the subject in the dark field image.

In the aforementioned X-ray phase imaging apparatus according to this aspect, the controller preferably controls the adjustment mechanism to adjust the relative position between the subject and the imaging grating so as to correspond to the dark field image in which the contrast of the region of interest is relatively high. According to this structure, when the contrast is insufficient, the relative position between the subject and the imaging grating can be adjusted such that the contrast is relatively high, and thus it is possible to easily acquire the dark field image having a sufficient level of contrast in the region of interest.

In the aforementioned X-ray phase imaging apparatus according to this aspect, the controller preferably causes a position of the region of interest to follow a change in the relative position between the subject and the imaging grating based on the contrast when changing the relative position between the subject and the imaging grating based on the acquired contrast. According to this structure, the position of the region of interest in the dark field image follows even when the subject moves with respect to the region of interest set in the dark field image, and thus the region of interest set in the dark field image does not deviate from the original region of interest in the subject.

In the aforementioned X-ray phase imaging apparatus according to this aspect, the controller preferably acquires the dark field image and information about the relative position between the subject and the imaging grating with respect to each of the plurality of relative positions between the subject and the imaging grating, and stores the dark field image and the information about the relative position in association with each other. According to this structure, the dark field image and the relative position are stored in association with each other, and thus even after the relative position between the subject and the imaging grating is shifted from the relative position between the subject and the imaging grating at the time of obtaining the dark field image, it is possible to adjust the relative position between the subject and the imaging grating again to the relative position between the subject and the imaging grating at the time of obtaining the dark field image and return the positional relationship. In other words, it is easy to adjust the relative position between the subject and the imaging grating again to a relative position between the subject and the imaging grating corresponding to a state in which a desired contrast is obtained.

In the aforementioned X-ray phase imaging apparatus according to this aspect, the controller preferably moves at least one of the subject and the imaging grating from the relative position between the subject and the imaging grating at which the contrast of the region of interest of the dark field image is determined to be maximum among a plurality of dark field images obtained in a first direction to the plurality of relative positions between the subject and the imaging grating in a second direction different from the first direction, and increases the contrast of the dark field image. According to this structure, it is possible to start movement of the relative position in the second direction from the relative positional relationship between the subject and the imaging grating where the contrast of the region of interest is the maximum in the first direction. Consequently, whether or not the contrast further increases due to movement (position variation) of the relative position in the second direction as compared with the maximum contrast already obtained for the first direction is examined such that the contrast can be efficiently increased.

In the aforementioned X-ray phase imaging apparatus according to this aspect, the controller preferably acquires the contrast of the dark field image based on an absolute value of a difference between an average value of pixel values in the region of interest and an average value of pixel values in a background region. According to this structure, it is possible to compare the pixel values in the region of interest with reference to the pixel values in the background region, which are substantially constant, and thus it is possible to easily and accurately acquire the contrast in the dark field image.

The aforementioned X-ray phase imaging apparatus according to this aspect preferably further includes at least one of an absorption grating disposed between the X-ray source and the detector, disposed behind the subject and the imaging grating as viewed from the X-ray source, and that detects the grating image generated by the imaging grating, and a light source grating disposed between the X-ray source and the detector, disposed in front of the subject and the imaging grating as viewed from the X-ray source, and that aligns phases of the X-rays such that the X-rays that have passed therethrough interfere with each other, and when adjusting the relative position between the subject and the imaging grating, the adjustment mechanism preferably maintains a relative position between at least one of the absorption grating and the light source grating and the imaging grating. According to this structure, the X-rays, the phases of which have been aligned by the light source grating, interfere with each other, and thus regardless of whether or not the phases of the X-rays at the time of irradiation from the X-ray source are aligned, it is possible to obtain a clear grating image by the imaging grating. Furthermore, the absorption grating absorbs the X-rays corresponding to the grating image generated by the imaging grating based on the shape of the grating image, and thus it is possible to obtain a clear grating image by the imaging grating. In addition, the relative position between the subject and the imaging grating is adjusted while the relative position between at least one of the absorption grating and the light source grating and the imaging grating is maintained, and thus it is possible to improve the contrast in the region of interest of the dark field image while maintaining a state in which a clear dark field image is obtained.

In the aforementioned X-ray phase imaging apparatus according to this aspect, the adjustment mechanism preferably adjusts the relative position between the subject and the imaging grating while maintaining relative positions of the X-ray source and the detector to the imaging grating. According to this structure, the relative position between the subject and the imaging grating is adjusted while the relative positions of the X-ray source and the detector to the imaging grating are maintained, and thus it is possible to improve the contrast in the region of interest of the dark field image while maintaining a state in which a clear dark field image is obtained.

In the aforementioned X-ray phase imaging apparatus according to this aspect, the controller preferably further acquires an absorption image representing a degree of X-ray absorption by the subject and a phase differential image representing a change in X-ray phase due to the subject. According to this structure, it is possible to acquire the absorption image and the phase differential image in addition to the dark field image from the obtained X-ray detection information, and thus it is possible to analyze the subject in a more multifaceted manner.

Effect of the Invention

As described above, according to the present invention, it is possible to sufficiently obtain the contrast in the region of interest of the subject in the dark field image.

MODES FOR CARRYING OUT THE INVENTION

An embodiment embodying the present invention is hereinafter described on the basis of the drawings.

(Structure of X-Ray Phase Imaging Apparatus)

The structure of an X-ray phase imaging apparatus 100 according to the present embodiment is now described with reference to FIGS. 1 and 2.

Figure 1:
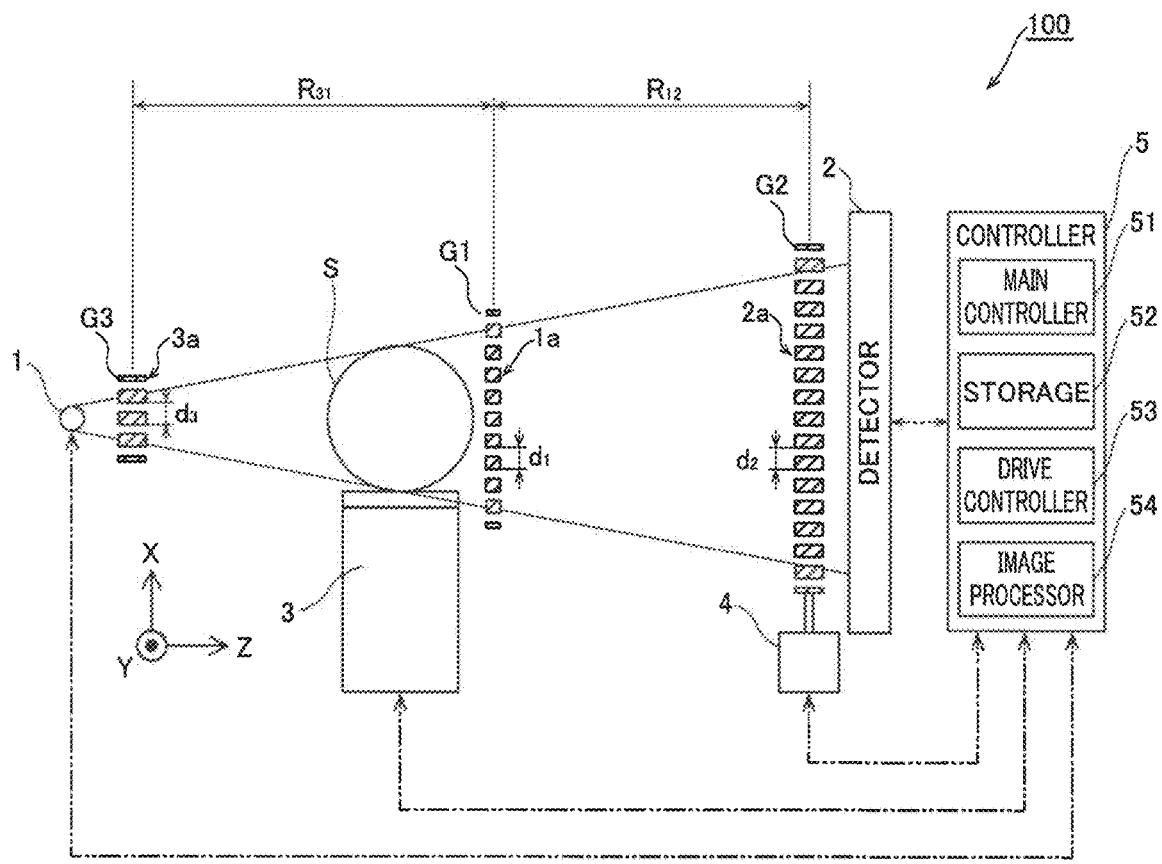
FIG. 1 is a diagram showing the overall structure of an X-ray phase imaging apparatus according to an embodiment of the present invention.

As shown in FIG. 1, the X-ray phase imaging apparatus 100 irradiates a subject S with X-rays to visualize or image an area to be imaged (an area to be visualized or an area to be image-captured) of the subject S. In addition, the X-ray phase imaging apparatus 100 includes an X-ray source 1 that radiates X-rays to a subject. The X-ray source 1 includes an X-ray tube, for example.

The X-ray phase imaging apparatus 100 includes an imaging grating G1 that generates a grating image by transmitting the X-rays radiated to the subject S from the X-ray source 1. When viewed from the X-ray source 1, the subject S is placed in front of the imaging grating G1 and behind a light source grating G3 (described below). The imaging grating G1 includes a phase type diffraction grating. For example, in the imaging grating G1, absorption members 1a made of gold plated on silicon, for example, and that absorb the X-rays are aligned at equal intervals in a one-dimensional direction (X direction) substantially perpendicular to the radiated X-rays. A certain phase difference (such as $\pi$ or $\pi/2$) is given between an X-ray that has passed through the absorption members 1a and an X-ray that has passed through transparent portions (portions in which there are not the absorption members). Furthermore, the absorption members 1a uniformly extend at a predetermined length in a Y direction, which is toward the rear side of the plane of the figure. The period (pitch) of the absorption members 1a in the X direction is $d_1$. The pitch $d_1$ is small enough that the radiated X-rays of a wavelength $\lambda$ cause interference due to diffraction. Thus, the diffracted X-rays transmitted through the imaging grating G1 generate interference fringes behind the imaging grating G1, and generate a self-image G0 in which the shape of the imaging grating G1 is enlarged at a certain distance interval. Such generation of the self-image G0 due to interference is called the Talbot effect. A position at which the self-image G0 is generated is called a Talbot distance. The Talbot distance is described in detail below. The self-image G0 is an example of a "grating image" in the claims.

The X-ray phase imaging apparatus 100 further includes a detector 2 that detects the X-rays that have passed through the imaging grating G1. The detector 2 includes a detection element (not shown) corresponding to each pixel in a plane perpendicular to an X-ray irradiation direction. The detection element converts the incident X-rays into an electric signal (detection signal) and outputs it to a controller 5 (described below). The detector 2 includes an FPD (flat panel detector), for example.

The X-ray phase imaging apparatus 100 includes an absorption grating G2 disposed between the X-ray source 1 and the detector 2, disposed behind the subject S and the imaging grating G1 as viewed from the X-ray source, and that detects the self-image G0 generated by the imaging grating G1. The absorption grating G2 includes an amplitude type diffraction grating. The absorption grating G2 is disposed at the Talbot distance at which the self-image G0 is generated. In addition, the absorption grating G2 includes a pattern (grating) of absorption members 2a of gold, for example, which absorb the X-rays. Thus, the X-rays incident on the positions of the absorption members 2a are absorbed (ideally blocked). The absorption members 2a are sufficiently long in the X-ray irradiation direction (Z direction), and each have a high aspect ratio to a pitch $d_2$. The absorption members 2a have the same shape as the self-image G0. Specifically, the period (pitch) of the absorption members in the X direction is $d_2$ and is equal to the period (pitch) of the self-image G0 in the X direction. Furthermore, the absorption members 1a uniformly extend at a predetermined length in the Y direction, which is toward the rear side of the plane of the figure. When the subject S exists on paths of the X-rays, the self-image G0 is distorted from the shape of the imaging grating G1 due to the influence of the subject S. The absorption grating G2 is superimposed on this distorted self-image G0 such that a moire image is generated due to the self-image G0 and absorption by the absorption grating G2. The period of the moire image is larger than the period of the self-image G0 (the period of the grating pattern of the imaging grating G1), and thus the resolution required for detection in the detector 2 decreases, and the distortion (a difference depending on the presence or absence of the subject S) of the self-image G0 can be easily detected.

The X-ray phase imaging apparatus 100 further includes the light source grating G3 disposed between the X-ray source 1 and the detector 2, disposed in front of the subject S and the imaging grating G1 as viewed from the X-ray source, and that aligns the phases of the X-rays such that the passed X-rays interfere with each other. The light source grating G3 includes an amplitude type diffraction grating. Absorption members 3a are members that remove X-rays not required for interference in order to generate the self-image G0. Even when the phases of the X-rays radiated from the X-ray source 1 are not aligned, the phases of the X-rays are aligned at the detection position by passing through the light source grating G3. This effect of aligning the phases of the passed X-rays is called the Lau effect. The period (pitch) of the light source grating G3 is $d_3$.

Here, the positional relationship between the X-ray source 1, the detector 2, the imaging grating G1, the absorption grating G2, and the light source grating G3 is described. As described above, the absorption grating G2 is disposed at or near a position at which the self-image G0 of the imaging grating G1 generated by the imaging grating G1 appears. The Talbot distance (the position at which the self-image G0 appears) $z_p$ is expressed by the following formula (1).

[Mathematical Formula 1]

$$z_p = p \frac{d_1^2}{\lambda} \frac{R_{31}}{R_{31} - p \frac{d_1^2}{\lambda}} \quad (1)$$

Here, $d_1$ represents the period (pitch) of the imaging grating G1, and $\lambda$ represents the wavelength of an X-ray. $R_{31}$ represents a distance between the light source grating G3 and the imaging grating G1 in the Z direction. Furthermore, p represents the Talbot order, and indicates the position at which the self-image G0 appears. The value of p corresponding to the self-image varies depending on the magnitude of the phases modulated by the imaging grating G1.

At this time, the period (pitch) $d_0$ of the self-image G0 in the X direction is expressed by the following formula (2).

[Mathematical Formula 2]

$$d_0 = \frac{R_{31} + z_p}{R_{31}} d_1 \quad (2)$$

Here, $R_{12}$ represents a distance between the imaging grating G1 and the absorption grating G2 in the Z direction. Therefore, the absorption grating G2 is disposed such that $R_{12} = z_p$ and $d_2 = d_0$. The light source grating G3 is disposed such that $d_3 : d_0 = R_{31} : z_p$ in order to align and overlap the phases of the self-image G0 generated by respective slits (transparent portions in which there are not the absorption members 3a) of the light source grating G3.

The X-ray phase imaging apparatus 100 further includes an adjustment mechanism 3 that changes and adjusts a relative position between the subject S and the imaging grating G1. The adjustment mechanism 3 also serves as a table on which the subject S is placed, and changes the relative position of the subject S to the imaging grating. Specifically, as shown in FIG. 2(a), the adjustment mechanism 3 includes a combination of electric positioning stages (any of stages shown in FIGS. 2(b), 2(c), 2(d), and 2(e)). Hereinafter, a shaded area in FIG. 2 is assumed to be a movable pedestal. A lifting stage shown in FIG. 2(b) can move the subject S in the X direction (upward-downward direction). A translation stage shown in FIG. 2(c) can move the subject S in the Y or Z direction (horizontal direction). A gonio stage (inclined stage) shown in FIG. 2(d) can move the subject S in a Y-axis rotation direction or a Z-axis rotation direction within a range of about 10 degrees to about 20 degrees. A rotary stage shown in FIG. 2(e) can move the subject S in an X-axis rotation direction within a range of at least 360 degrees. These positioning stages have stepping motors and piezo actuators, and the position of the subject S can be adjusted at intervals of high precision of micrometers or 0.01 degrees. These positioning stages are combined such that as shown in FIG. 2(f), the subject S can be moved in (1) an X translation direction, (2) a Y translation direction, (3) a Z translation direction, (4) the X-axis rotation direction, (5) the Y-axis rotation direction, and (6) the Z-axis rotation direction. Note that the adjustment mechanism 3 may include at least one positioning stage corresponding to the translation or rotation direction. Furthermore, a single positioning stage capable of moving the subject S in a plurality of directions may be used.

The X-ray phase imaging apparatus 100 further includes a movement mechanism 4 that moves the absorption grating G2 up and down in the X direction with respect to the imaging grating G1. The movement mechanism 4 includes a lifting stage, for example.

In the present embodiment, as shown in FIG. 1, the X-ray phase imaging apparatus 100 includes the controller 5. The controller 5 generates a dark field image Iv representing a change in X-ray sharpness between the case in which the subject S is present and the case in which the subject S is not present, an absorption image Ia representing the degree of X-ray absorption, and a phase differential image Id representing a change in X-ray phase based on an X-ray signal detected by the detector 2 with respect to each of a plurality of relative positions (imaging positions) between the subject S and the imaging grating G1 changed by the adjustment mechanism 3.

Specifically, the controller 5 includes an information processor such as a PC (personal computer), and exchanges signals (information) with the X-ray source 1, the detector 2, the adjustment mechanism 3, and the movement mechanism 4. More specifically, the controller 5 includes a main controller 51 such as a CPU (central processing unit), a storage 52 such as an HDD (hard disk drive) and a memory, a drive controller 53, and an image processor 54. The image processor 54 may be a dedicated arithmetic processor for image processing or may function as the image processor 54 by causing the CPU to execute an image processing program. Furthermore, a dedicated device for image processing may be provided as the image processor 54. Arrows shown by two-dot chain lines indicate that signal exchange is being performed.

The main controller 51 causes the PC to function as the controller 5 of the X-ray phase imaging apparatus 100 by executing a control program stored in the storage 52.

The storage 52 stores various programs executed by the main controller 51, the drive controller 53, and the image processor 54 as well as data of an X-ray image I captured by the detector 2 and the positions of the imaging grating G1 and the subject S (the positional parameters of the adjustment mechanism 3 and the movement mechanism 4) at the time of capturing the X-ray image I.

The drive controller 53 controls X-ray irradiation from the X-ray source 1, the position (imaging position) of the adjustment mechanism 3, and the position (grating position) of the movement mechanism 4. Furthermore, the drive controller 53 outputs information (positional parameters) about the position (imaging position) of the adjustment mechanism 3 and the position (grating position) of the movement mechanism 4 to the storage 52 and stores the same in the storage 52.

The image processor 54 adds image processing to the X-ray image I. Furthermore, the image processor 54 acquires the absorption image Ia representing the degree of X-ray absorption by the subject S, the phase differential image Id representing the change in X-ray phase due to the subject S, and the dark field image Iv representing the change in X-ray sharpness between the case in which the subject S is present and the case in which the subject S is not present from a plurality of X-ray images I, and outputs the same to the storage 52.

(Acquisition of Absorption Image, Phase Differential Image, and Dark Field Image)

Figure 3:
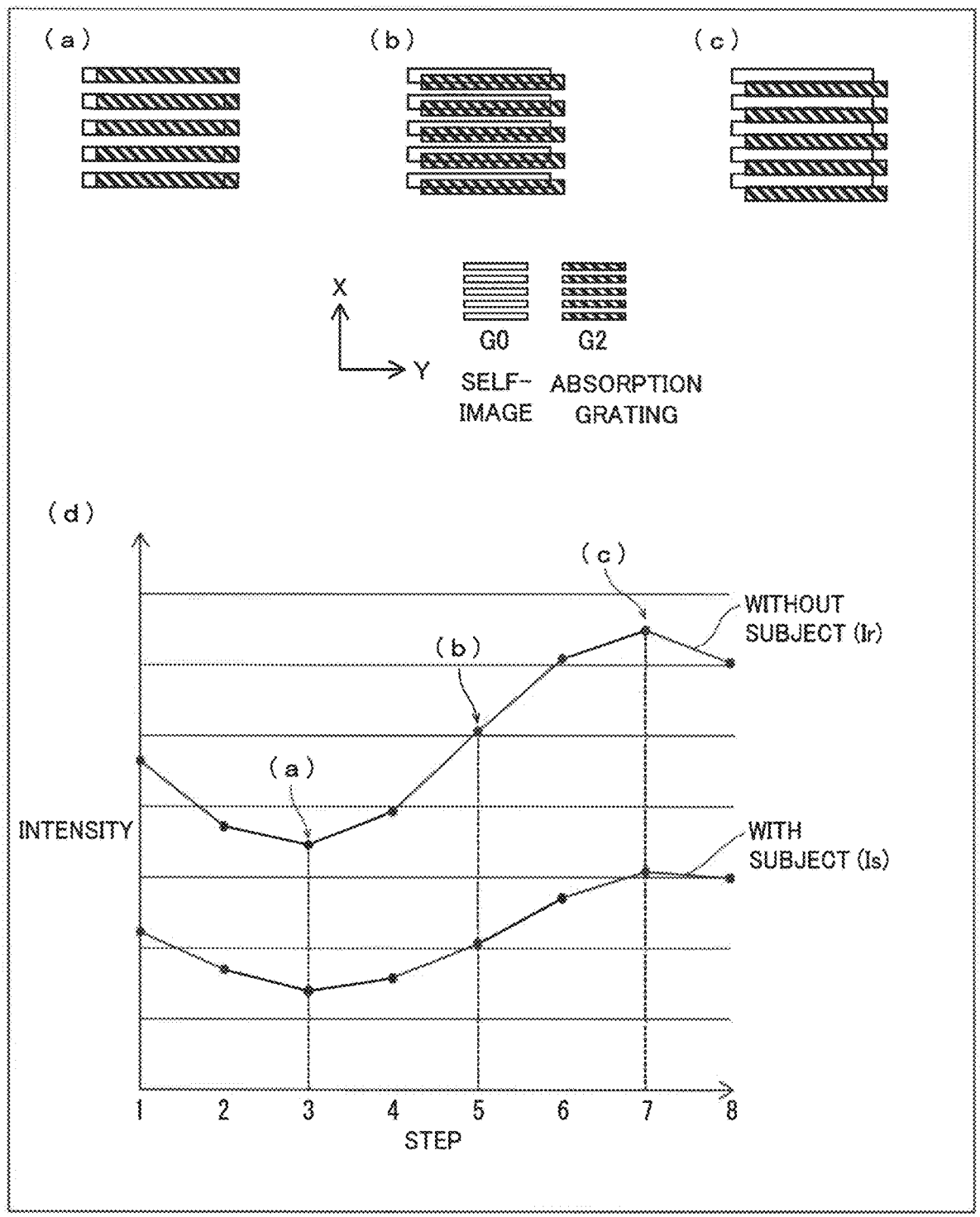
FIG. 3 is a diagram illustrating the positional relationship between a self-image and a grating and step curves according to the embodiment of the present invention.
Figure 4:
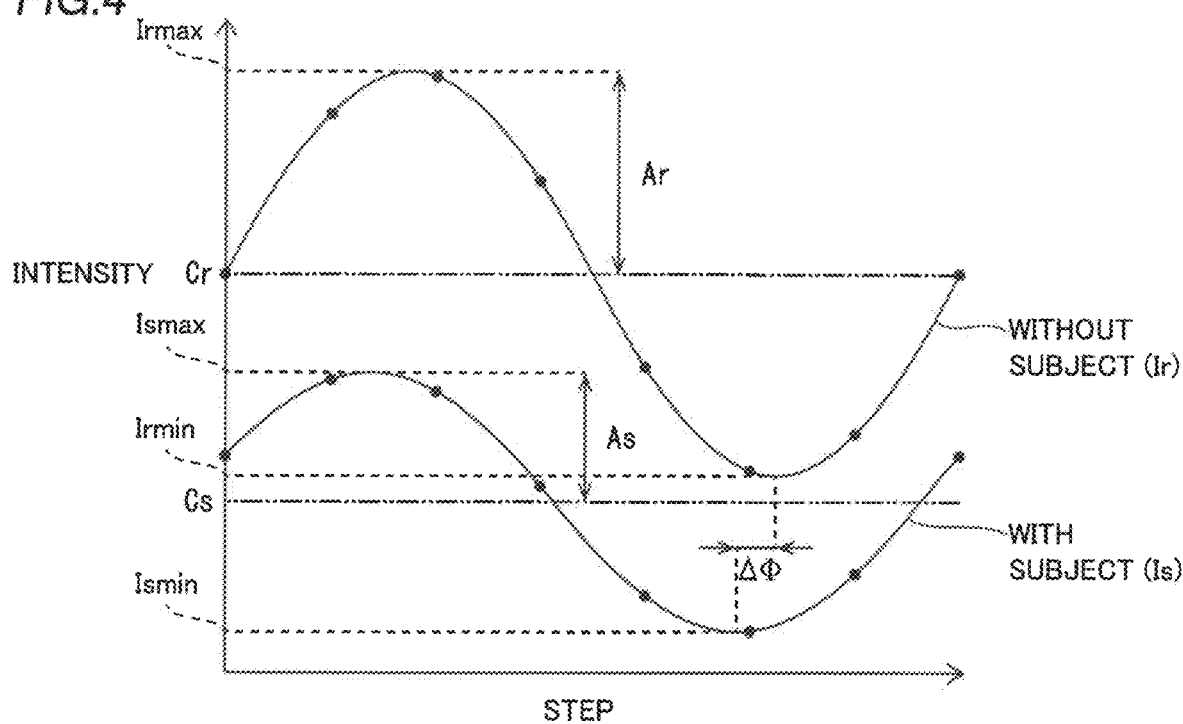
FIG. 4 is a graph of step curves according to the embodiment of the present invention.

Hereinafter, acquisition of the absorption image Ia, the phase differential image Id, and the dark field image Iv is described with reference to FIGS. 3 to 5. The absorption image Ia, the phase differential image Id, and the dark field image Iv are obtained by comparing an X-ray image Ir in the case in which there is no subject S and an X-ray image Is in the case in which the subject S is placed.

The X-ray image Ir and the X-ray image Is are captured a plurality of times while the position (grating position) of the absorption grating G2 is changed. For comparison, the X-ray images Ir and Is are captured at the same corresponding gating position. FIGS. 3(a), 3(b), and 3(c) show the positional relationship between the self-image G0 generated by the imaging grating G1 and the absorption grating G2. FIGS. 3(a) to 3(c) are diagrams as viewed in an X-ray imaging direction. In the self-image G0, the insides of white rectangles correspond to portions in which the X-rays strengthen each other by interference, and the remaining portions correspond to portions in which the X-rays weaken each other by interference. As shown in FIGS. 3(a) to 3(c), the self-image G0, which is a grating image at the Talbot distance $z_p$, has a light and dark striped pattern of X-rays that reflect the shape of the imaging grating G1. In the absorption grating G2, the insides of shaded rectangles correspond to the absorption members 2a.

The absorption grating G2 substantially overlaps the self-image G0. Therefore, as shown in FIG. 3(a), the self-image G0 and the absorption members of the absorption grating G2 are disposed in an overlapping manner such that it is possible to block the X-rays of the self-image G0. For the sake of clarity, the absorption grating G2 is slightly shifted in a right-left direction (Y direction). The absorption grating G2 is moved in the upward-downward direction (X direction) at regular intervals to capture the X-ray image Ir and the X-ray image Is at the grating position. FIG. 3(b) shows a state in which the absorption grating G2 is shifted downward so as to overlap the self-image G0 by approximately half. FIG. 3(c) shows a state in which the absorption grating G2 is further shifted downward so as not to overlap the self-image G0.

FIG. 3(d) shows a step curve of the pixel value (a luminance value representing the magnitude of the X-ray detection amount, for example) of one pixel of each of the X-ray image Ir and the X-ray image Is corresponding to each grating position (each step), acquired in a state in which the subject S is on the paths of the X-rays and in a state in which the subject S is not on the paths of the X-rays. The vertical axis represents the intensity of the detected X-rays. The horizontal axis represents the grating position (step) number (moving distance) of imaging. Such a step curve is acquired for all the pixels. The pixel values are acquired at eight steps (eight grating positions), respectively. FIGS. 3(a), 3(b), and 3(c) correspond to the numbers (moving distances) 3, 5, and 7 of the grating positions (steps) indicated by dotted lines, respectively. In FIGS. 3(a), 3(b), and 3(c), the pixel values decrease in this order due to the X-ray absorption in the absorption grating G2. Furthermore, the grating position of FIG. 3(a) corresponds to the step with the minimum pixel value, and the grating position of FIG. 3(c) corresponds to the step with the maximum pixel value. Distortion (a difference depending on the presence or absence of the subject S) is also generated in the shape of the step curve between the case in which the subject S is present and the case in which the subject S is not present. In order not to move the subject S with respect to the adjustment mechanism 3 during imaging, the step curve in a state in which the subject S is placed is acquired after the step curve in a state in which there is no subject S is acquired.

The two step curves in the case in which there is no subject S (X-ray image Ir) and in the case in which there is the subject S (X-ray image Is) obtained as described above are compared for each pixel. FIG. 4 shows step curves obtained for a certain pixel. Average intensities Cr and Cs, amplitudes Ar and As, and a phase difference MO are obtained from the respective step curves in the case in which there is no subject S (r) and in the case in which there is the subject S (s). Thus, in each pixel, the ratio T of the average intensity, the magnitude MO of the phase change, and the ratio v of the sharpness (the amplitude normalized by the average intensity) are obtained. T, ΔΦ, and v are expressed by the following formulas (3) to (5).

[Mathematical Formula 3]

$$T = \frac{Cs}{Cr} \quad (3)$$

[Mathematical Formula 4]

$$\frac{\partial \Phi}{\partial x} = const \times \Delta\Phi \quad (4)$$

[Mathematical Formula 5]

$$v = \frac{Vs}{Vr} = \frac{\left(\frac{As}{Cs}\right)}{\left(\frac{Ar}{Cr}\right)} = \frac{\left(\frac{Ismax - Ismin}{Ismax + Ismin}\right)}{\left(\frac{Irmax - Irmin}{Irmax + Irmin}\right)} \quad (5)$$

Here, Irmax and Irmin are the maximum value and the minimum value of the step curve in the case in which the subject S is not present. In addition, Ismax and Ismin are the maximum value and the minimum value of the step curve in the case in which the subject S is present.

Figure 5:
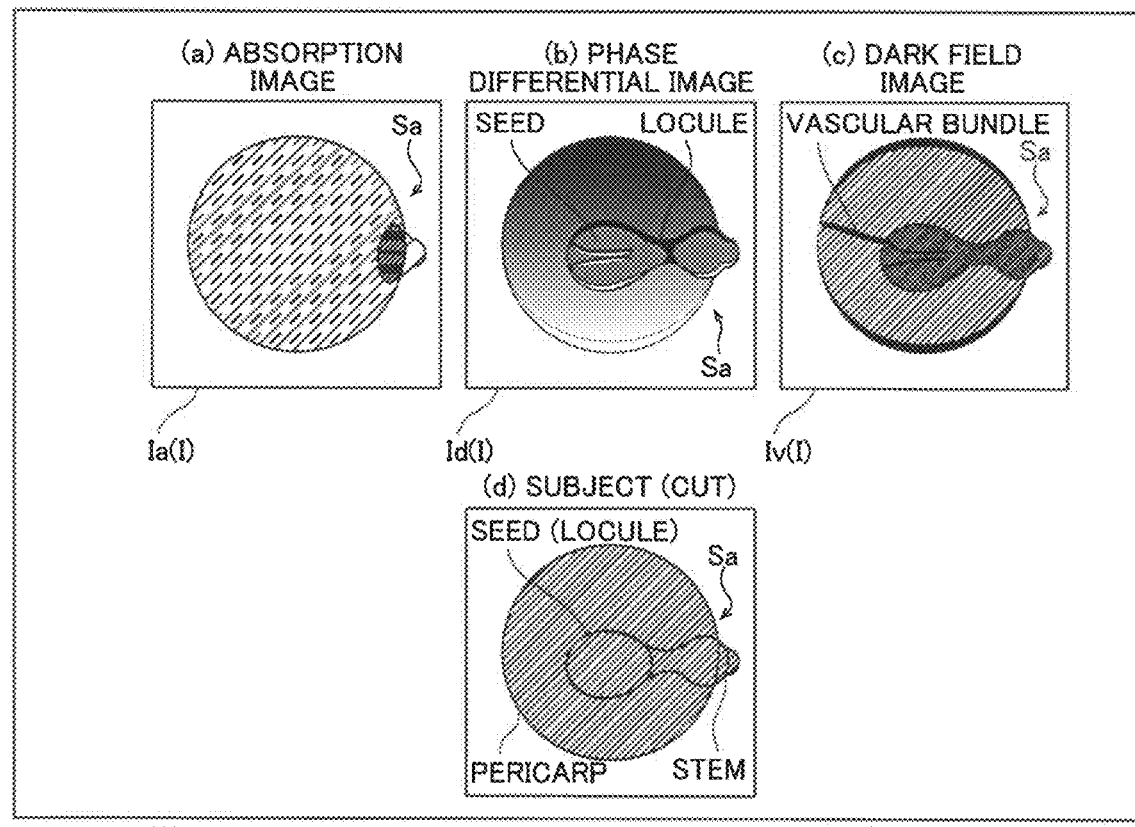
FIG. 5 is a diagram illustrating an absorption image, a phase differential image, and a dark field image according to the embodiment of the present invention.

From these values, an absorption image Ia, a phase differential image Id, and a dark field image Iv of a fruit Sa (an example of the subject S) as shown in FIG. 5 are obtained. The absorption image Ia shown in FIG. 5(a) is obtained by imaging the ratio T of the average intensity in each pixel. The absorption image Ia represents the absorption degree of X-rays absorbed by the subject. The phase differential image Id shown in FIG. 5(b) is obtained by imaging the magnitude MO of the phase change in each pixel. The phase change occurs due to a difference in the refractive index of a medium, and thus the phase differential image Id is obtained based on information about a relatively shallow position such as a boundary surface of the medium is obtained. The fact that the pericarp is imaged black at the upper end of the fruit Sa and is imaged white at the lower end reflects the fact that the magnitude of the phase change is acquired, taking plus/minus into consideration. The dark field image Iv shown in FIG. 5(c) is obtained by imaging the ratio v of the sharpness at each pixel. Due to the scattering (small angle scattering) of the X-rays due to the microstructure of the subject, the amount of X-rays incident on the detector 2 and having the aligned phases is relatively reduced as compared with the case in which the subject S is not present. Consequently, the degree of interference of the X-rays having the aligned phases decreases, and thus a difference between the maximum value and the minimum value of the step curve (a difference in degree between strengthening and weakening) decreases, and the sharpness decreases.

FIG. 5(c) shows a cross-section of the fruit Sa cut perpendicular to the imaging direction after imaging. The degree of absorption depends on the weight of a nucleus, and thus it is small in light elements and is difficult to image. However, the phase change and the scattering are large in light elements as compared with the degree of absorption, and thus they can be imaged. In fact, it can be seen that information about the structure of the seed, pericarp, vascular bundle, locule, etc. that cannot be obtained from the absorption image Ia is obtained from the phase differential image Id and the dark field image Iv. Particularly, in the dark field image Iv, scattering by the small cells of the pericarp, seed, and vascular bundle or the porous microstructures (microparticles), for example, is imaged. Furthermore, in the dark field image Iv, scattering by a structure (microparticle) having the same size as the wavelengths λ of the X-rays is well imaged.

(Contrast of Dark Field Image)

Figure 6:
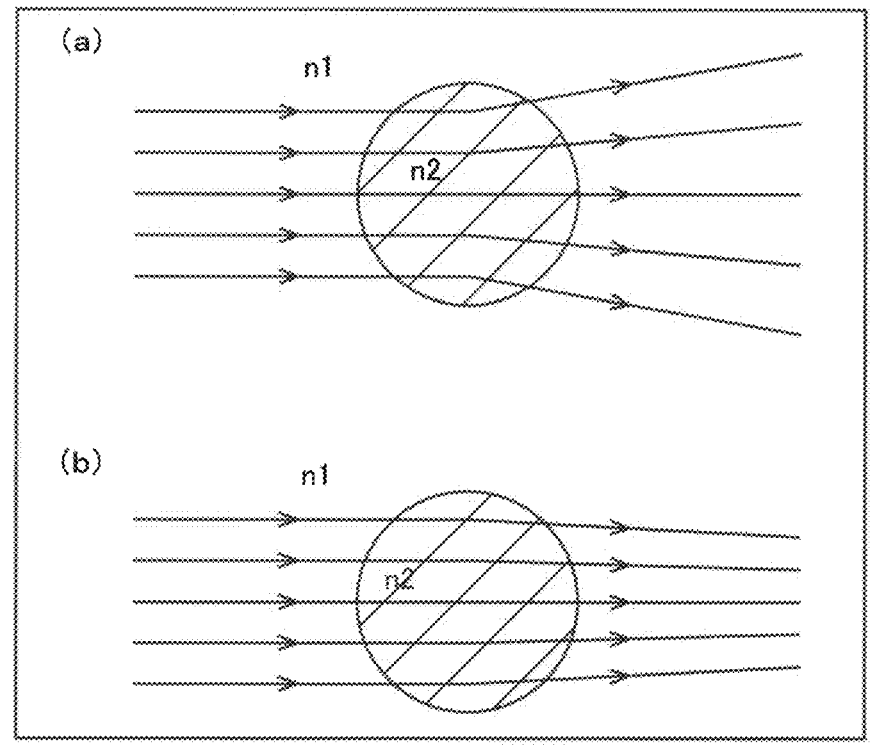
FIG. 6 is a diagram illustrating scattering by a microparticle.
Figure 7:
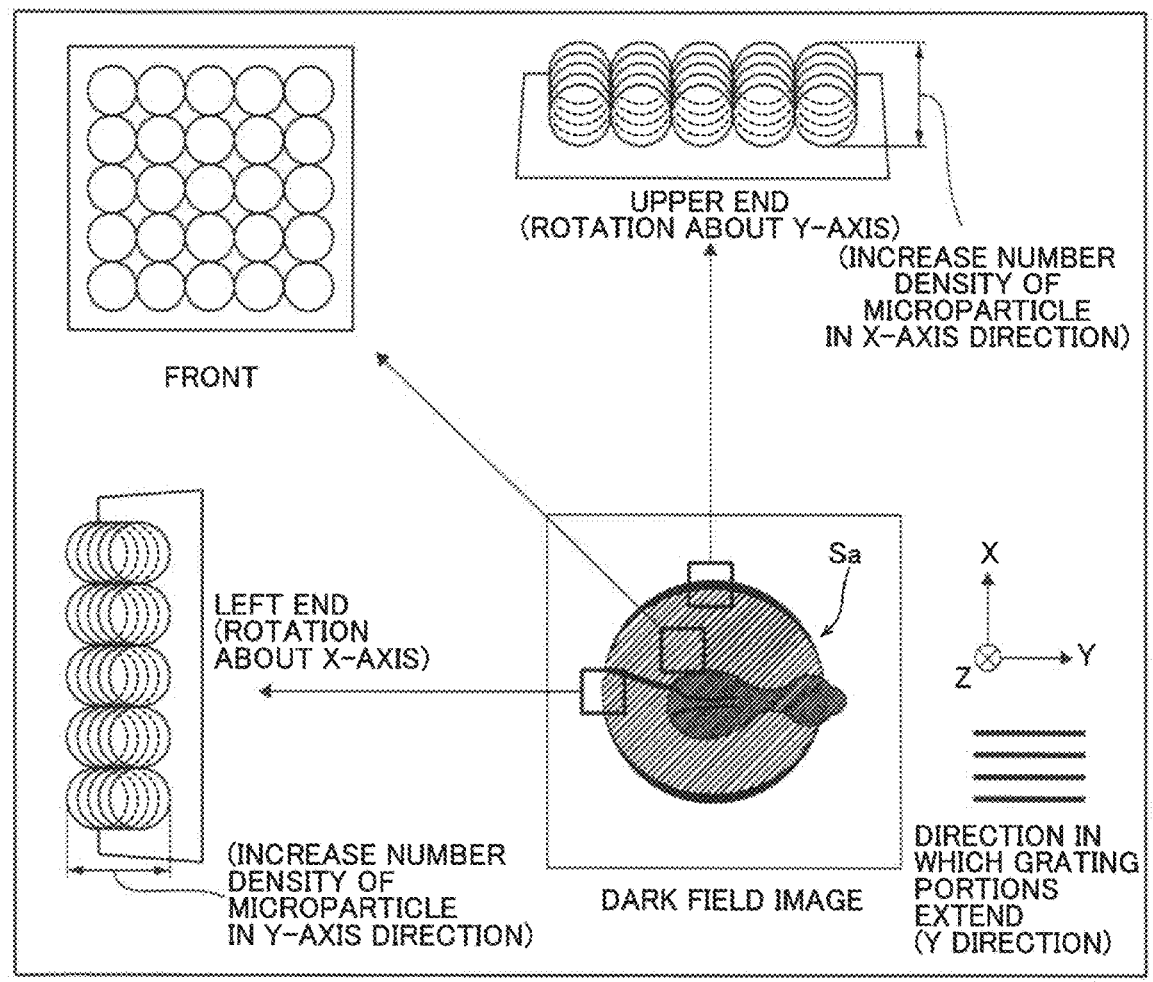
FIG. 7 is a diagram illustrating the relationship between contrast appearance in the dark field image and a direction in which grating portions extend and contrast adjustment according to the embodiment of the present invention.

The contrast of the dark field image Iv is now described in more detail with reference to FIGS. 6 and 7.

First, scattering (small angle scattering) by the microparticles is described with reference to FIG. 6. As shown in FIG. 5, when one microparticle is approximated as a spherical shape, the substantially parallel flux of the X-rays incident on the microparticle is scattered as shown in FIG. 6(a) or FIG. 6(b). Here, $n_1$ represents the refractive index of the medium outside the microparticle, and $n_2$ represents the refractive index of the microparticle. In FIG. 6(a), scattering occurs so as to diffuse from the center of the microparticle (sphere). In FIG. 6(b), scattering occurs so as to converge on the center of the microparticle (sphere). However, also in FIG. 6(b), the flux of the incident X-rays is diffused at a sufficient distance. Which scattering occurs in FIG. 6(a) and FIG. 6(b) depends on the refractive indices $n_1$ and $n_2$ and the wavelengths λ of the X-rays. In general, it is known that in a region in which the incident light is visible, the scattering in FIG. 6(a) occurs, and in a region in which the incident light becomes X-rays (radiation), the scattering in FIG. 6(b) occurs. Furthermore, in both FIG. 6(a) and FIG. 6(b), the incident light is scattered at a larger angle as it approaches the edge (boundary) of the microparticle.

Next, scattering by the pericarp of the fruit Sa is described with reference to FIG. 7. As the pericarp is closer to the surface, it contains more microparticles, and thus scattering of X-rays is more likely to occur. The pericarp in the dark field image Iv in FIG. 7 (the same as in FIG. 4) is clearly imaged at the upper and lower ends (ends in the X direction), but it is hardly imaged at the right and left ends (ends at the Y direction). A difference in sensitivity between these scatterings depends on the directions of grating portions of the imaging grating G1 and the absorption grating G2.

Here, it is assumed that the pericarp is a thin layer of the microparticle, and only scattering by the edge of the microparticle is considered. Furthermore, the microparticle layer of the pericarp at the upper end and the microparticle layer of the pericarp at the left end are substantially the same as structures obtained by rotating the microparticle layer of the pericarp at the front about a Y-axis and an X-axis. When the X-rays are incident on the microparticle layer of the pericarp from the front, the number density (edge amount) of the microparticle in a region through which the X-rays pass is small, and thus X-ray scattering only slightly occurs. On the other hand, when the X-rays are obliquely incident on the microparticle layer of the pericarp, the number density (edge amount) of the microparticle in the region through which the X-rays pass is relatively large, and thus the proportion of scattered X-rays also increases. That is, in a portion corresponding to the outline of the fruit Sa, the proportion of scattered X-rays becomes large.

At the end of the pericarp, it is believed that almost the same amount of scattering occurs although the direction is different. However, the distortion (difference) of the self-image G0 can be detected only when it occurs in the X direction perpendicular to a direction in which the grating portions extend (the imaging grating G1 and the absorption grating G2) extend. Therefore, the distortion (a difference in sharpness due to scattering, for example) of the self-image G0 generated in the Y direction, which is the direction in which the grating portions extend, is not detected.

Even if the imaging grating G1, the absorption grating G2, and the light source grating G3 are properly disposed according to the Talbot distance, as described above, the contrast of the dark field image Iv is not always obtained properly depending on the relationship between the direction of X-ray scattering generated by the subject S and the direction in which the grating portions extend. Therefore, the controller 5 controls the adjustment mechanism 3 to adjust the relative position between the subject S and the imaging grating G1 in order to sufficiently obtain the contrast of the dark field image Iv.

(Contrast Adjustment of Dark Field Image)

Figure 8:
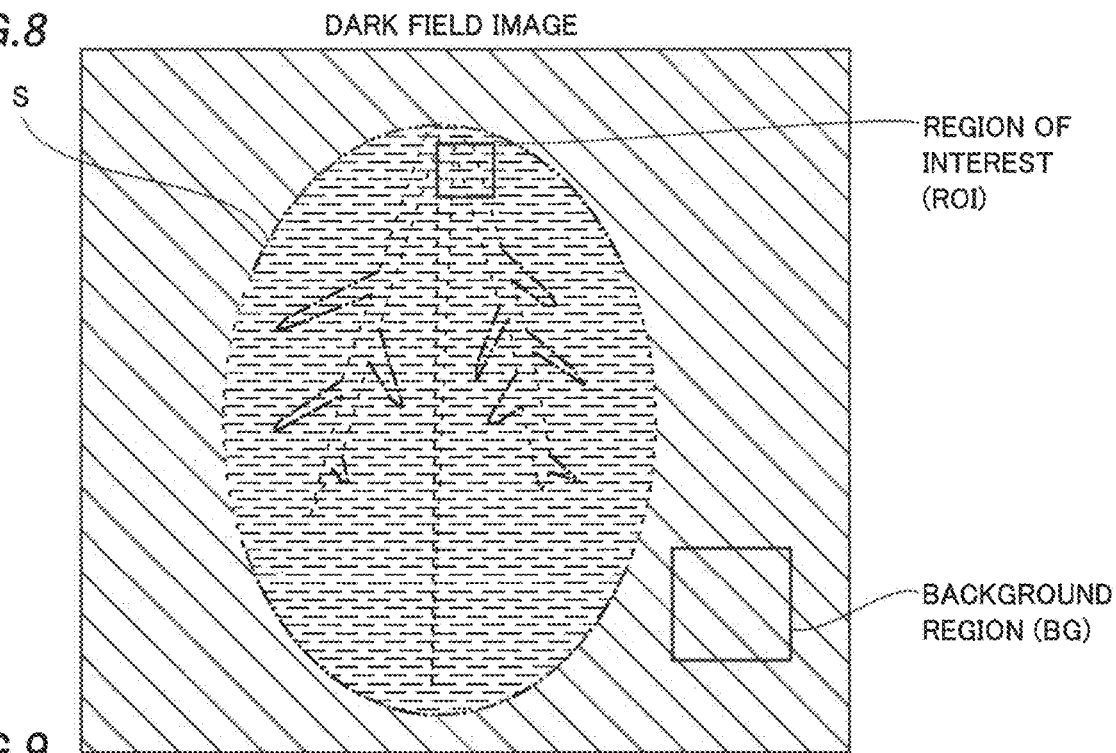
FIG. 8 is a diagram showing examples of a region of interest and a background region according to the embodiment of the present invention.

Hereinafter, the contrast adjustment of the dark field image Iv is described with reference to FIGS. 8 and 9. When it is assumed that the relative positions of the X-ray source 1, the detector 2, the imaging grating G1, the absorption grating G2, and the light source grating G3 have already been adjusted such that the self-image is properly imaged, the relative positions of them are fixed in the contrast adjustment of the dark field image. However, upward and downward movement (relative movement to the imaging grating G1 in the X direction) of the absorption grating G2 for obtaining the step curves is excluded.

That is, when adjusting the relative position between the subject S and the imaging grating G1, the adjustment mechanism 3 maintains the relative position between both the absorption grating G2 and the light source grating G3 and the imaging grating G1.

The adjustment mechanism 3 adjusts the relative position between the subject S and the imaging grating G1 while maintaining the relative positions of the X-ray source 1 and the detector 2 to the imaging grating G1.

In the present embodiment, the controller 5 acquires the contrast of a region of interest ROI in each dark field image Iv, and controls the adjustment mechanism 3 to adjust the relative position between the subject S and the imaging grating G1 based on the acquired contrast.

The controller 5 acquires the contrast of the dark field image Iv based on the absolute value of a difference between the average value $I_{ROI}$ of pixel values in the region of interest ROI and the average value $I_{BG}$ of pixel values in a background region BG.

Specifically, the controller 5 (image processor 54) acquires the dark field image Iv, the absorption image Ia, and the phase differential image Id in a state in which the subject S is placed on a certain fixed position (a relative position including an angle with respect to the imaging grating G1). At this time, the controller 5 acquires the contrast in the region of interest ROI set in the subject S in the dark field image Iv. At this time, the contrast is obtained by the absolute value of the difference between the average value $I_{ROI}$ of the pixel values (a luminance value representing the magnitude of the sharpness ratio, for example) of pixels in the region of interest ROI set in the subject S and the average value $I_{BG}$ of the pixel values of pixels in the background region BG, which is a region in which the subject S is not reflected, as shown in FIG. 8. That is, when the contrast in the region of interest ROI is α, it is calculated by the following formula (6).

[Mathematical Formula 6]

$$\alpha = |I_{ROI} - I_{BG}| \quad (6)$$

Based on the acquired contrast in the region of interest ROI, the relative position between the subject S and the imaging grating G1 is changed in the adjustment mechanism 3 such that the contrast in the region of interest ROI becomes sufficiently large. Furthermore, the dark field image Iv, the absorption image Ia, and the phase differential image Id are acquired at a new relative position between the subject S and the imaging grating G1. The larger the region of interest ROI and the background region BG, the smaller the influence due to the unevenness (noise) of irradiation from the X-ray source, and the better the S/N ratio.

The controller 5 controls the adjustment mechanism 3 to adjust the relative position between the subject S and the imaging grating G1 so as to correspond to the dark field image Iv in which the contrast of the region of interest ROI is relatively high.

Specifically, the controller 5 controls the adjustment mechanism 3 to adjust the relative position between the subject S and the imaging grating G1 such that the contrast in the region of interest ROI of the dark field image Iv becomes larger at the new relative position between the subject S and the imaging grating G1 than that at the position before the change.

When changing the relative position between the subject and the imaging grating G1 based on the acquired contrast of each dark field image Iv, the controller 5 causes the position of the region of interest ROI to follow the change in the relative position between the subject S and the imaging grating G1 based on the contrast.

Specifically, the positional parameter of the table of the adjustment mechanism 3 on which the subject S is placed is controlled by the controller 5. Thus, when changing the positional parameter of the table of the adjustment mechanism 3 on which the subject S is placed, the controller 5 (drive controller 53) knows how the placed subject S moves with respect to the captured X-ray image I. Therefore, the controller 5 can cause the region of interest ROI set in the subject S to follow the movement of the subject S in the X-ray image I via the positional parameter.

The controller 5 acquires the dark field image Iv and information about the relative position between the subject S and the imaging grating G1 with respect to each of a plurality of relative positions between the subject S and the imaging grating G1, and stores the dark field image Iv and the information about the relative position in association with each other.

Specifically, the controller 5 (storage 52) acquires the positional parameter of the adjustment mechanism 3, which is the relative position of the subject S to the imaging grating G1, in order to obtain a plurality of dark field images Iv each time X-ray imaging is performed, and stores the positional parameter in association with the X-ray image I. Furthermore, the controller 5 (storage 52) acquires the positional parameter of the movement mechanism 4, which is the relative position (upward-downward position) of the absorption grating G2 to the imaging grating G1, for obtaining the step curves each time X-ray imaging is performed, and stores the positional parameter in association with the X-ray image I. Note that each position parameter may not be acquired every imaging but may be acquired every time the positional parameter is changed.

The controller 5 moves at least one of the subject S and the imaging grating G1 from a relative position between the subject S and the imaging grating G1 at which the contrast in the region of interest of the dark field image is determined to be the maximum among a plurality of dark field images obtained in a first direction to a plurality of relative positions between the subject S and the imaging grating G1 in a second direction different from the first direction, and increases the contrast of the dark field image Iv.

Figure 2:
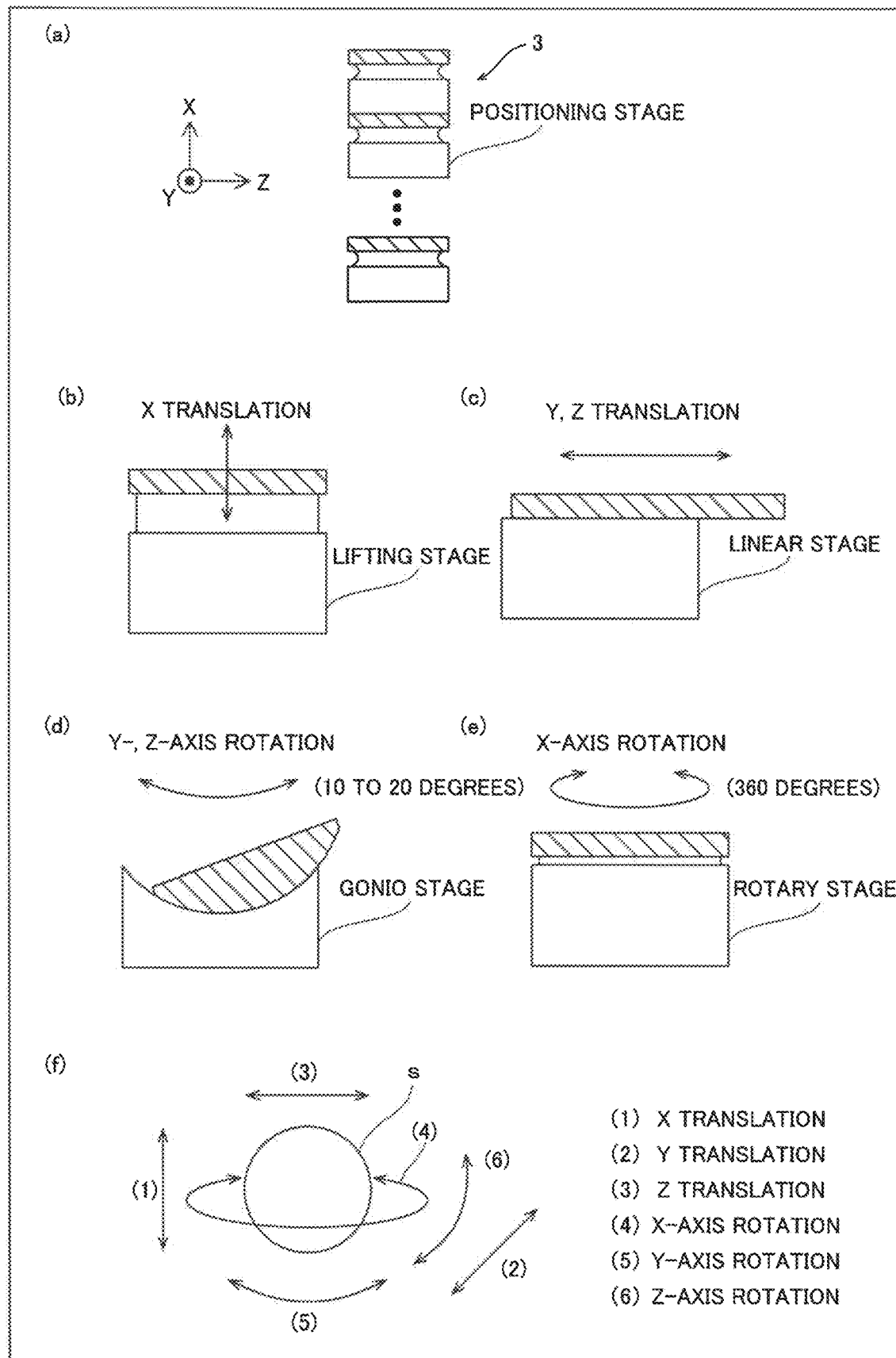
FIG. 2 is a schematic view illustrating an adjustment mechanism according to the embodiment of the present invention.

Specifically, there is the movement of the relative position of the subject S to the imaging grating G1 by the adjustment mechanism 3 in up to six directions (see FIG. 2). When a user inputs the movement direction and the movement range, the controller 5 determines one movement direction (Z-axis rotation direction, for example) for efficiently increasing the contrast in the region of interest ROI, based on the priority order according to the designation by the user or the advance setting. At the initial position of the subject S, the dark field image Iv, the absorption image Ia, and the phase differential image Id (hereinafter referred to as the three images) are acquired by changing the position of the absorption grating G2. Thereafter, in the determined direction and range, the relative position of the subject S to the imaging grating G1 is moved at a certain step (number of times), and the three images are acquired at each position. The number of steps is determined from the imaging time and the accuracy desired to obtain the three images, for example.

Next, after acquiring the three images based on one movement direction (Z-axis rotation, for example), the controller 5 calculates the contrast in the region of interest ROI of each of a plurality of dark field images Iv obtained at the relative positions. Then, a dark field image Ivmax with the maximum contrast is specified, and the subject S is returned to the corresponding position. That is, the controller 5 controls the adjustment mechanism 3 to adjust the positional parameter corresponding to the dark field image Ivmax again.

At this time, the contrast in the region of interest ROI of the subject S is the maximum in the measurement range in the first direction (one direction described above; Z-axis rotation direction, for example). Therefore, the controller 5 changes the position of the subject S relative to the imaging grating G1 in the second direction (Y-axis rotation direction, for example), and acquires the contrast for each position. Then, the controller 5 compares the contrast obtained due to the movement in the second direction with the maximum contrast obtained in the first direction, and moves the subject S to a newly highest contrast position. Furthermore, the controller 5 performs the same imaging for a third, fourth, . . . direction (X translation movement, for example), and terminates the imaging in all input or set directions.

When an image is captured by changing the position of the subject S, the movement amount of the subject S is determined from the movement accuracy of the adjustment mechanism 3, the size of the region of interest of the subject, the time taken for imaging, etc. As an example, when the subject S is rotated within a range of 5 degrees in increments of 0.1 degrees, the number of imaging times of the dark field image Iv is 50 times.

Figure 9:
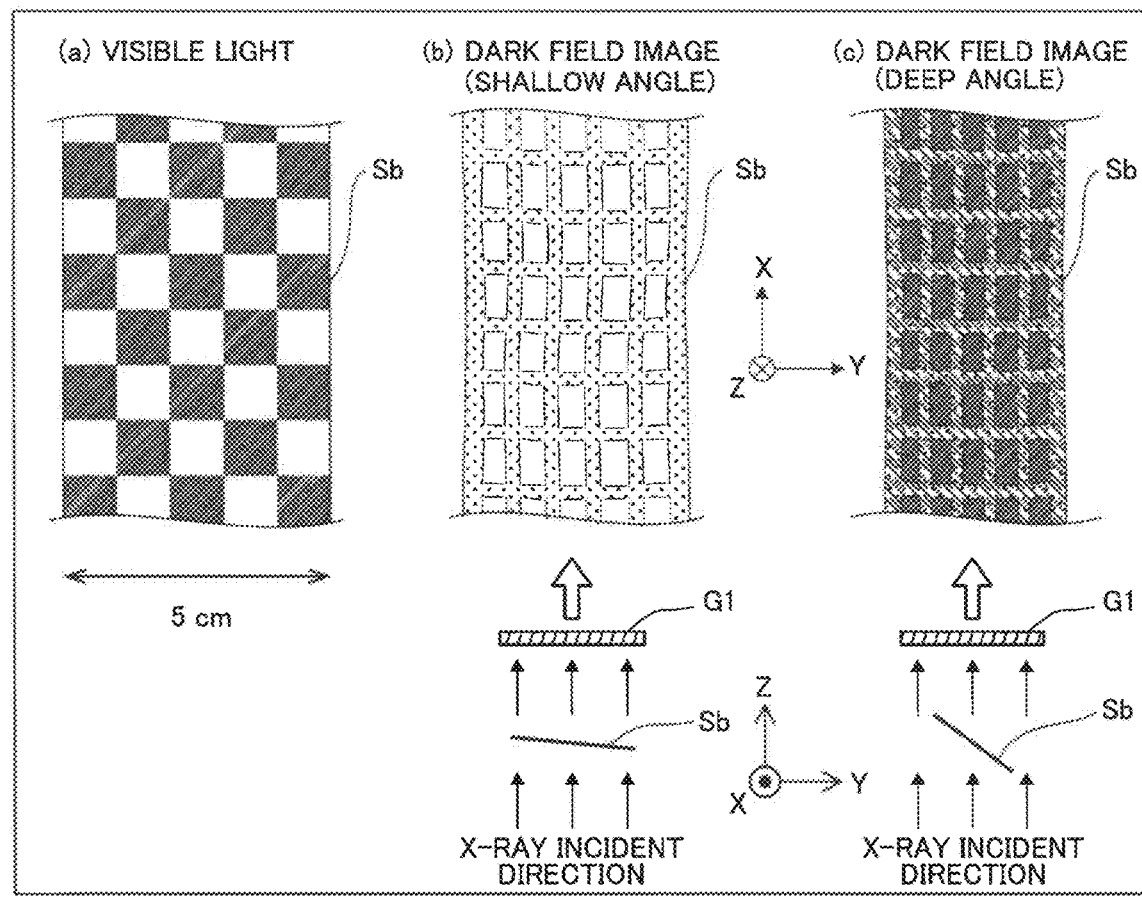
FIG. 9 is a diagram showing an example of movement of a subject in contrast adjustment of the dark field image according to the embodiment of the present invention.

FIG. 9 is a diagram of a fiber material Sb (an example of the subject S) obtained braiding fine fibers. As shown in FIG. 9(*a*), the fiber material Sb has regions in which the fibers are braided in different directions (right and left or up and down), and looks like a checkered pattern in a visible light region. Here, when it is assumed that X-rays are made incident on the fiber material, the direction of scattering differs according to a direction in which the fibers extend. Therefore, the dark field image Iv also reflects the checkered pattern. At this time, the angle of the fiber material Sb is changed with respect to the incident X-rays such that the incident angle with respect to the direction of the fibers changes. Thus, the rate at which X-ray scattering occurs increases or decreases, and thus the contrast in the region of interest ROI of the dark field image Iv changes.

When the fiber material Sb is placed so as to have a shallow angle with respect to the X-ray incident angle, the fiber structure does not appear so clearly, as shown in FIG. 9(*b*). On the other hand, when the fiber material Sb is placed so as to have a deep angle with respect to the X-ray incident angle, the fiber structure clearly appears, as shown in FIG. 9(*c*). That is, the fiber material Sb is moved in the X-axis rotation direction such that it is possible to increase the contrast of the dark field image. Thus, the relative position of the fiber material Sb (subject S) to the X-ray irradiation direction (i.e. the position relative to the imaging grating G1) is changed such that it is possible to increase the contrast of the dark field image Iv. When a region of fibers that extend in a direction opposite to the direction in which the grating portions extend, where the contrast of the fiber material Sb is lowered, is imaged, the fiber material Sb may be rotated in a plane perpendicular to the X-ray irradiation direction (moved in the Z-axis rotation direction), for example.

Similarly, when it is desired to image scattering by the pericarp of a left end of the fruit Sa (see FIG. 7), for example, the fruit Sa is moved by 90 degrees in the Z-axis rotation direction, and the pericarp of a portion to be observed (region of interest) is adjusted to the upper end or the lower end. When it is desired to image scattering by the pericarp of a frontal portion of the fruit Sa, for example, the fruit Sa is moved in the Y-axis rotation direction, and the pericarp of the portion to be observed is adjusted to the upper end or the lower end.

The X-ray phase imaging apparatus 100 according to the present embodiment acquires the dark field image Iv, the absorption image Ia, and the phase differential image Id by performing the imaging and the position adjustment as described above, and maximizes the contrast of the dark field image Iv.

Hereinafter, X-ray image acquisition processing and dark field image contrast adjustment processing by the controller 5 are described based on flowcharts shown in FIGS. 10 and 11.

(X-Ray Image Acquisition Processing)

Figure 10:
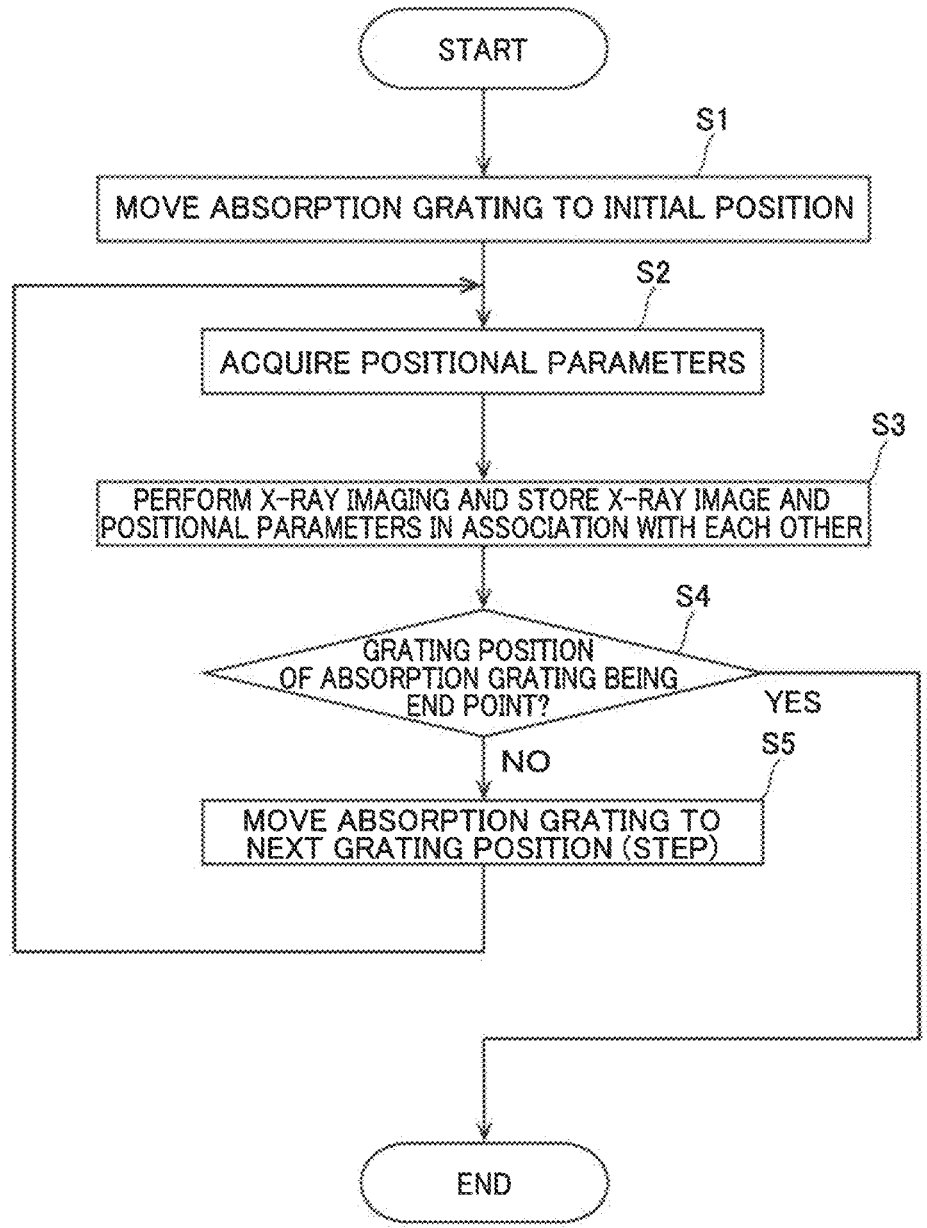
FIG. 10 is a flowchart illustrating X-ray image acquisition processing according to the embodiment of the present invention.
Figure 11:
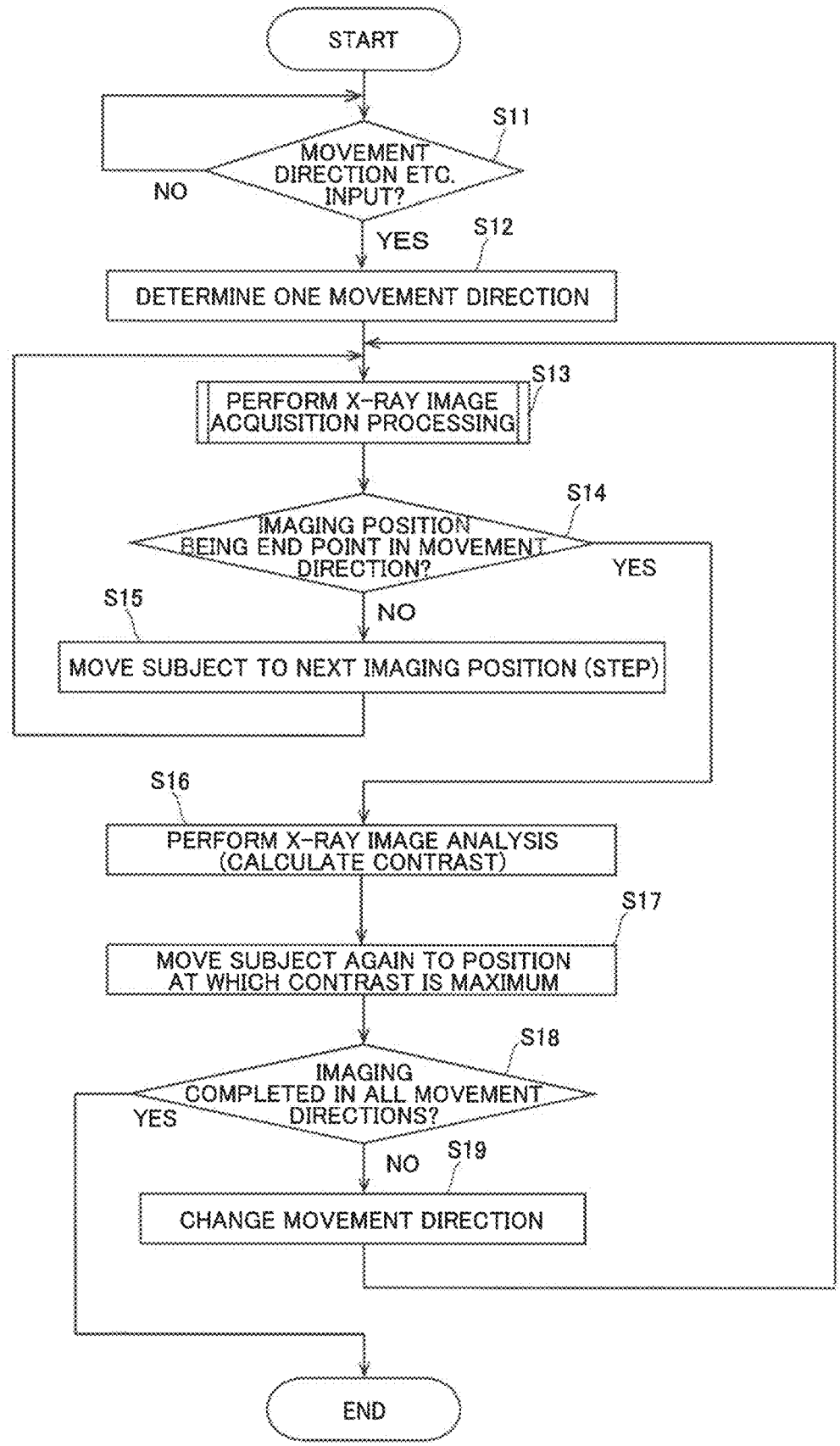
FIG. 11 is a flowchart illustrating dark field image contrast adjustment processing according to the embodiment of the present invention.

First, the X-ray image acquisition processing for acquiring the dark field image Iv, the absorption image Ia, and the phase differential image Id at one fixed relative position between the subject S and the imaging grating G1 is described based on FIG. 10. Note that the procedure for capturing the X-ray image Ir in the case in which the subject S is not placed is the same as the following procedure. After all the X-ray images Ir in the case in which the subject is not present are acquired in first, the X-ray image Is in the case in which the subject is present is acquired.

In the X-ray phase imaging apparatus 100, when X-ray imaging is started, the controller 5 controls the movement mechanism 4 to move the absorption grating G2 to its initial position in step S1, and advances to step S2. The initial position is a position corresponding to one of the end points of the step curves, for example.

In step S2, the controller 5 acquires the information about the positional parameters of the adjustment mechanism 3 and the movement mechanism 4, and advances to step S3. The positional parameters are control parameters of the adjustment mechanism 3 and the movement mechanism 4 for determining the position (imaging position) of the subject S and the position (grating position) of the absorption grating G2.

In step S3, the controller 5 controls the X-ray source 1 to radiate the X-rays, and acquires the data of the X-ray image I detected by the detector 2. Then, the controller 5 stores the acquired data of the X-ray image I and the various positional parameters in association with each other, and advances to step S4.

In step S4, the controller 5 terminates the X-ray image acquisition processing when the grating position (imaging step) of the absorption grating G2 is the end point (YES). In step S4, when the grating position (imaging step) to be imaged of the absorption grating G2 still remains, and it is not the end point (NO), the controller 5 advances to step S5.

In step S5, the controller 5 moves the absorption grating G2 to the next grating position (imaging step), and returns to step S2.

As described above, the X-ray phase imaging apparatus 100 according to the present embodiment can acquire a plurality of X-ray images I that serve as the basis of the step curves required to acquire the dark field image Iv, the absorption image Ia, and the phase differential image Id by repeating the operations in step S2 to step S5.

(Dark Field Image Contrast Adjustment Processing)

Next, the dark field image contrast adjustment processing for acquiring the dark field image Iv, the absorption image Ia, and the phase differential image Id while changing the relative position between the subject S and the imaging grating G1 and maximizing the contrast in the region of interest ROI of the acquired dark field image Iv is described with reference to FIG. 11.

When the dark field image contrast adjustment processing is started, the controller 5 advances to step S12 when there is an input of the movement direction and the movement range or an instruction for imaging within a preset range (YES) in step S11. When there is no input of the movement direction etc., the controller 5 returns to step S11.

In step S12, the controller 5 determines one movement direction (such as the Z-axis rotation direction) based on the input by the user or the advance setting, and advances to step S13. The movement direction to be input or set may be at least one direction.

In step S13, the controller 5 performs the X-ray image acquisition processing (see step S1 to step S5 in FIG. 10) and advances to step S14.

When the imaging position (the relative position of the subject S to the imaging grating G1, the step) to be imaged is the end point in the movement direction (YES) in step S14, the controller 5 advances to step S16. When the imaging position (step) is not the end point in the movement direction (NO), and the imaging position to be imaged still remains, the controller 5 advances to step S15.

In step S15, the controller 5 controls the adjustment mechanism 3 to move the subject S to the next imaging position (step), and returns to step S13.

In step S16, the controller 5 acquires (calculates) the contrasts in the regions of interest ROI of the plurality of dark field images Iv obtained at the imaging positions, and advances to step S17.

In step S17, the controller 5 moves the subject S again to a position corresponding to the dark field image Ivmax with the maximum contrast in all movement directions among the acquired contrasts in the regions of interest ROI of the dark field images Iv, and advances to step S18.

In step S18, the controller 5 acquires whether or not imaging has been completed in all planned movement directions, and terminates the dark field image contrast adjustment processing when imaging has been completed (YES). When imaging has not been completed in all the planned movement directions (NO), and imaging to be performed in another movement direction remains, the controller 5 advances to step S19.

In step S19, the controller 5 sets a new movement direction for the subject S based on the input by the user or the advance setting, and returns to step S13.

As described above, the X-ray phase imaging apparatus 100 according to the present embodiment can perform adjustment so as to maximize the contrast of the dark field image Iv by repeating the operations in step S13 to step S19.

Advantageous Effects of Embodiment

According to the embodiment of the present invention, the following advantageous effects are achieved.

According to the present embodiment, as described above, the controller 5 generates the dark field image Iv representing the change in X-ray sharpness between the case in which the subject S is present and the case in which the subject S is not present based on the X-ray signal detected by the detector 2 with respect to each of the plurality of relative positions between the subject S and the imaging grating G1 changed by the adjustment mechanism 3 to acquire the contrast of the region of interest ROI in the dark field image Iv, and adjusts the relative position between the subject S and the imaging grating G1 based on the acquired contrast. Accordingly, the relative position between the subject S and the imaging grating G1 is adjusted based on the contrast of the subject S in the dark field image Iv such that it is possible to sufficiently obtain the contrast in the region of interest ROI of the subject S in the dark field image Iv.

According to the present embodiment, as described above, the controller 5 controls the adjustment mechanism 3 to adjust the relative position between the subject S and the imaging grating G1 so as to correspond to the dark field image Iv in which the contrast of the region of interest ROI is relatively high. Accordingly, when the contrast is insufficient, the relative position between the subject S and the imaging grating G1 can be adjusted such that the contrast is relatively high, and thus it is possible to easily acquire the dark field image Iv having a sufficient level of contrast in the region of interest ROI.

According to the present embodiment, as described above, the controller 5 causes the position of the region of interest ROI to follow the change in the relative position between the subject S and the imaging grating G1 based on the contrast when changing the relative position between the subject S and the imaging grating G1 based on the acquired contrast of the dark field image Iv. Accordingly, the position of the region of interest ROI in the dark field image Iv follows even when the subject S moves with respect to the region of interest ROI set in the dark field image Iv, and thus the region of interest ROI set in the dark field image Iv does not deviate from the original region of interest ROI in the subject S.

According to the present embodiment, as described above, the controller 5 acquires the dark field image Iv and the information about the relative position between the subject S and the imaging grating G1 (the positional parameters of the adjustment mechanism 3 and the movement mechanism 4) with respect to each of the plurality of relative positions between the subject S and the imaging grating G1, and stores the dark field image Iv and the information about the relative position (the positional parameters of the adjustment mechanism 3 and the movement mechanism 4) in association with each other. Accordingly, the dark field image Iv and the relative position are stored in association with each other, and thus even after the relative position between the subject S and the imaging grating G1 is shifted from the relative position between the subject S and the imaging grating G1 at the time of obtaining the dark field image Iv, it is possible to adjust the relative position between the subject S and the imaging grating G1 again to the relative position between the subject S and the imaging grating G1 at the time of obtaining the dark field image Iv and return the positional relationship. In other words, it is easy to adjust the relative position between the subject S and the imaging grating again to a relative position between the subject S and the imaging grating corresponding to a state in which a desired contrast is obtained.

According to the present embodiment, as described above, the controller 5 moves at least one of the subject S and the imaging grating G1 from the relative position between the subject S and the imaging grating at which the contrast in the region of interest of the dark field image Iv is determined to be the maximum among the plurality of dark field images Iv obtained in the first direction to the plurality of relative positions between the subject S and the imaging grating G1 in the second direction different from the first direction, and increases the contrast of the dark field image Iv. Accordingly, it is possible to start movement of the relative position in the second direction from the relative positional relationship between the subject S and the imaging grating G1 where the contrast of the region of interest ROI is the maximum in the first direction. Consequently, whether or not the contrast further increases due to movement (position variation) of the relative position in the second direction as compared with the maximum contrast already obtained for the first direction is examined such that the contrast can be efficiently increased.

According to the present embodiment, as described above, the controller 5 acquires the contrast of the dark field image Iv based on the absolute value of the difference between the average value of the pixel values (the luminance value representing the magnitude of the sharpness ratio, for example) in the region of interest ROI and the average value of the pixel values in the background region BG. Accordingly, it is possible to compare the pixel values in the region of interest ROI with reference to the pixel values in the background region BG, which are substantially constant, and thus it is possible to easily and accurately acquire the contrast of the region of interest ROI in the dark field image.

According to the present embodiment, as described above, the X-ray phase imaging apparatus 100 further includes the absorption grating G2 disposed between the X-ray source 1 and the detector 2, disposed behind the subject S and the imaging grating G1 as viewed from the X-ray source 1, and that detects the grating image (the self-image G0, for example) generated by the imaging grating G1, and the light source grating G3 disposed between the X-ray source 1 and the detector 2, disposed in front of the subject S and the imaging grating G1 as viewed from the X-ray source 1, and that aligns the phases of the X-rays such that the passed X-rays interfere with each other. Furthermore, when adjusting the relative position between the subject S and the imaging grating G1, the adjustment mechanism 3 maintains the relative position between both the absorption grating G2 and the light source grating G3 and the imaging grating G1. Accordingly, the X-rays, the phases of which have been aligned by the light source grating G3, interfere with each other, and thus regardless of whether or not the phases of the X-rays at the time of irradiation from the X-ray source 1 are aligned, it is possible to obtain a clear grating image (the self-image G0, for example) by the imaging grating G1. Furthermore, the absorption grating G2 absorbs the X-rays corresponding to the grating image generated by the imaging grating G1 based on the shape of the grating image, and thus it is possible to obtain a clear grating image (the self-image G0, for example) by the imaging grating G1. In addition, the relative position between the subject S and the imaging grating G1 is adjusted while the relative position between both the absorption grating G2 and the light source grating G3 and the imaging grating G1 is maintained, and thus it is possible to improve the contrast in the region of interest ROI of the dark field image Iv while maintaining a state in which a clear dark field image Iv is obtained.

According to the present embodiment, as described above, the adjustment mechanism 3 adjusts the relative position between the subject S and the imaging grating G1 while maintaining the relative positions of the X-ray source 1 and the detector 2 to the imaging grating G1. Accordingly, the relative position between the subject S and the imaging grating G1 is adjusted while the relative positions of the X-ray source 1 and the detector 2 to the imaging grating G1 are maintained, and thus it is possible to improve the contrast in the region of interest ROI of the dark field image Iv while maintaining a state in which a clear dark field image Iv is obtained.

According to the present embodiment, as described above, the controller 5 further acquires the absorption image Ia representing the degree of X-ray absorption by the subject S and the phase differential image Id representing the change in X-ray phase due to the subject S. Accordingly, it is possible to acquire the absorption image Ia and the phase differential image Id in addition to the dark field image Iv from the obtained X-ray detection information (the step curves based on the plurality of X-ray images Is and Ir), and thus it is possible to analyze the subject S in a more multifaceted manner.

Modified Examples

The embodiment disclosed this time must be considered as illustrative in all points and not restrictive. The scope of the present invention is not shown by the above description of the embodiment but by the scope of claims for patent, and all modifications (modified example) within the meaning and scope equivalent to the scope of claims for patent are further included.

The same structures as those of the embodiment described above are denoted by the same reference numerals in the figures, and description thereof is omitted.

For example, continuous imaging is performed once in one direction when the contrast in the region of interest ROI of the dark field image Iv is maximized in the aforementioned embodiment, the present invention is not restricted to this. According to the present invention, continuous imaging may be performed a plurality of times in one direction. In this case, the controller 5 moves the subject S every large unit (10 μm or 1 degree, for example) in one direction to perform imaging, and once acquires the position at which the contrast is the maximum. After that, the controller 5 moves the subject S every new small unit (1 μm or 0.1 degrees, for example) around the position at which the contrast is the maximum to perform imaging, and acquires again the position at the contrast is the maximum. In this case, the first direction and the second direction are the same as each other, for example. Thus, the number of times of imaging can be reduced, and thus it is possible to reduce the dose of X-rays and shorten the imaging time.

While the example in which the acquired contrasts of the dark field images Iv are compared after imaging in one movement direction is completed has been shown in the aforementioned embodiment, the present invention is not restricted to this. According to the present invention, the contrast of the dark field image Iv may be acquired and compared in real time in the course of imaging in one movement direction. In this case, the controller 5 changes the relative position between the subject S and the imaging grating G1 such that the contrast in the region of interest ROI of the dark field image Iv increases. Specifically, an X-ray image is captured while the subject S is moved in the first direction, and a position (the maximum value of the contrast) at which the contrast has changed from increase to decrease is acquired as the maximum value (local maximum value) in the course of imaging. In addition, the controller 5 aborts the movement in the first direction. Then, the controller 5 starts imaging in the second direction from the position (the maximum value of the contrast) at which the contrast has changed from increase to decrease in the first direction, and similarly, the controller 5 adjusts the position of the subject S such that the contrast increases. Thus, the position at which the dark field image Iv increases is acquired without imaging all the imaging ranges, and thus it is possible to reduce the dose of X rays and shorten the imaging time.

While the example in which when the contrast image of the dark field image is maximized, one having the maximum contrast in the region of interest ROI among all the dark field images Iv is acquired has been shown in the aforementioned embodiment, the present invention is not restricted to this. According to the present invention, the controller 5 may select one having the maximum contrast only from among the dark field images Iv with relatively good visibility of the region of interest ROI. Furthermore, the controller 5 may adjust the contrast further taking into consideration the imaging conditions of the absorption image Ia and the phase differential image Id.

While the example in which the contrast in the region of interest ROI of the dark field image Iv is acquired (calculated) based on the absolute value of the difference between the average value $I_{ROI}$ of the pixel values in the region of interest ROI and the average value $I_{BG}$ of the pixel values in the background region BG has been shown in the aforementioned embodiment, the present invention is not restricted to this. According to the present invention, the controller 5 may acquire the contrast by another method (an acquisition method using the absolute value of a difference between the median values of the pixel values in the regions, for example).

Figure 12:
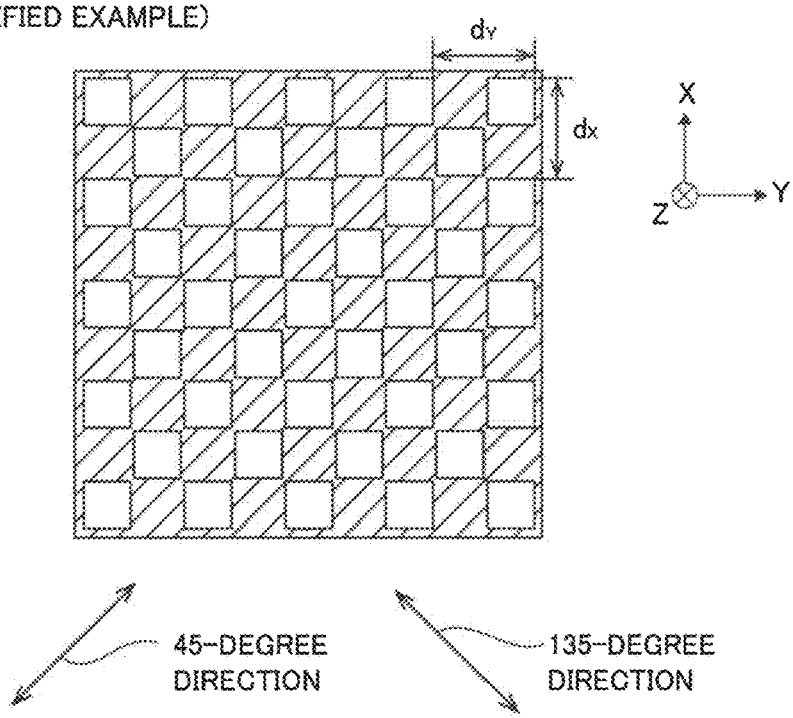
FIG. 12 is a schematic view showing a two-dimensional grating according to a modified example of the embodiment of the present invention.

While the example in which the grating portions of the gratings (the imaging grating G1, the absorption grating G2, and the light source grating G3) extend only in one dimension has been shown in the aforementioned embodiment, the present invention is not restricted to this. According to the present invention, as shown in FIG. 12, the grating portions of the gratings may extend in two dimensions (two directions). Here, a period (pitch) $d_X$ in the X direction (upward-downward direction) and a period (pitch) $d_Y$ in the Y direction (horizontal direction) are properly set. In this case, it is possible to simultaneously detect the distortion (a difference depending on the presence or absence of the subject) of a grating image in the X direction and the Y direction. However, even in this case, the distortion of the grating image in oblique directions (a 45-degree direction and a 135-degree direction) is hardly detected. Therefore, even when the gratings each having a two-dimensional structure are used, the contrast of the dark field image Iv is adjusted. If the directions of the grating portions are one-dimensional, it is possible to obtain a bright image with a small amount of X-ray absorption. If the directions of the grating portions are two-dimensional, it is possible to detect the distortion of the grating image in the two directions as described above. In addition, the shapes of the gratings are not limited to the above shapes, and grating portions each having a periodic structure may be widely used.

While the example in which the self-image G0 is captured has been shown in the aforementioned embodiment, the present invention is not restricted to this. According to the present invention, a grating image corresponding to the Talbot order p that does not generate the self-image G0 may be captured. Also in this case, a similar dark field image Iv, a similar absorption image Ia, and a similar phase differential image Id can be acquired from a specific grating image.

While the example in which the adjustment mechanism 3 is used to adjust the contrast of the dark field image Iv has been shown in the aforementioned embodiment, the present invention is not restricted to this. According to the present invention, using the adjustment mechanism 3, imaging may be performed while the imaging range of the subject S is changed, and a plurality of obtained X-ray images I may be connected to each other. Thus, a larger range of the subject S can be captured.

While the example in which image analysis is performed by a so-called fringe scanning method for acquiring the three images (the dark field image Iv, the absorption image Ia, and the phase differential image Id) based on the step curves obtained by moving the absorption grating G2 in the upward-downward direction (the X direction perpendicular to the grating portions) has been shown in the aforementioned embodiment, the present invention is not restricted to this. According to the present invention, the three images may be obtained by image analysis using a Fourier transform method. In the Fourier transform method, the absorption grating G2 is slightly rotated (Z-axis rotated) within a plane horizontal to the imaging grating G1. Thus, moire fringes due to the rotation are generated in the X-ray image I obtained by the detector 2. The controller 5 can acquire the three images by performing Fourier transform and inverse Fourier transform on these moire fringes due to the rotation to perform analysis. In the Fourier transform method, although the resolution of the obtained image is limited to the period of moire fringes, three images can be acquired from one moire image, and thus the imaging time can be shortened.

While the example in which the number of grating positions (steps) of the absorption grating G2 to be imaged in order to obtain the step curves is set to 8 has been shown in the aforementioned embodiment, the present invention is not restricted to this. According to the present invention, the number of grating positions of the absorption grating G2 to be imaged may not be 8.

Figure 13:
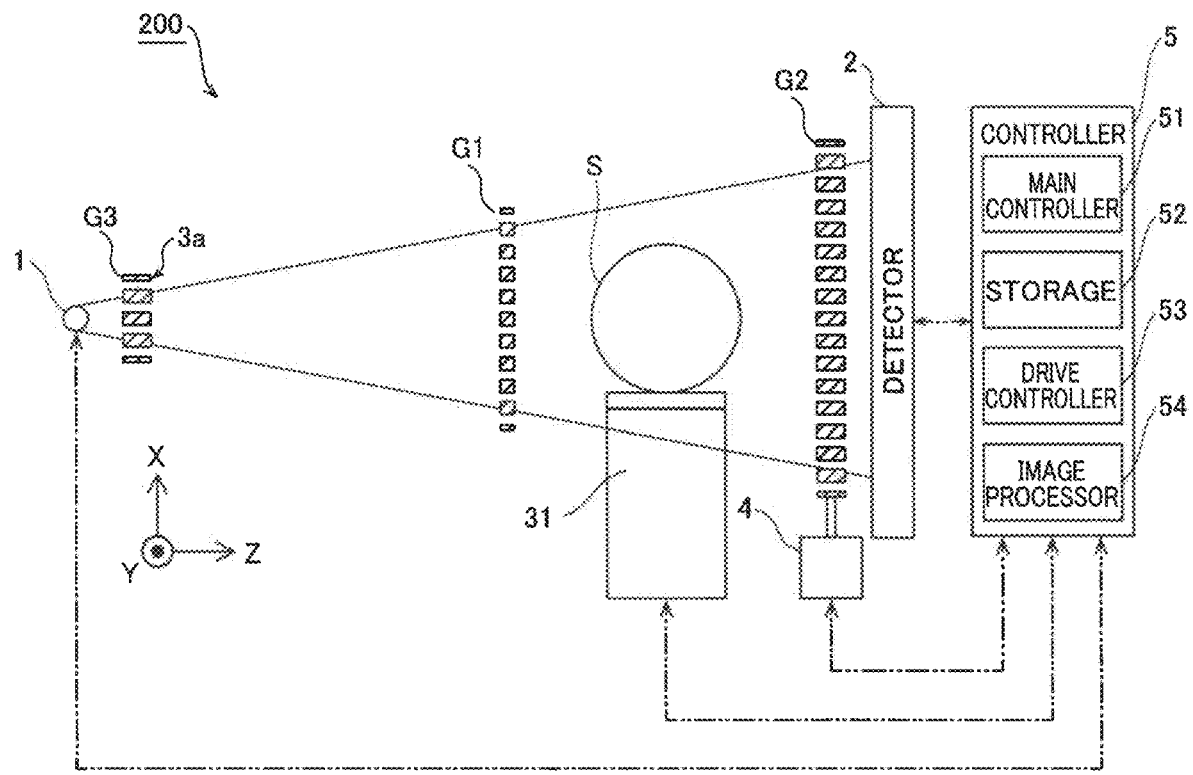
FIG. 13 is a diagram showing the overall structure of an X-ray phase imaging apparatus in which the arrangement of a subject S is changed according to a modified example of the embodiment of the present invention.

While the example in which the subject S is placed in front of the imaging grating G1 as viewed from the X-ray source 1 has been shown in the aforementioned embodiment, the present invention is not restricted to this. According to the present invention, the subject S may be placed behind the imaging grating G1 and in front of the absorption grating G2 as viewed from the X-ray source. Specifically, as shown in FIG. 13, in an X-ray phase imaging apparatus 200, the subject S and an adjustment mechanism 31 are disposed between the imaging grating G1 and the absorption grating G2, for example.

Figure 14:
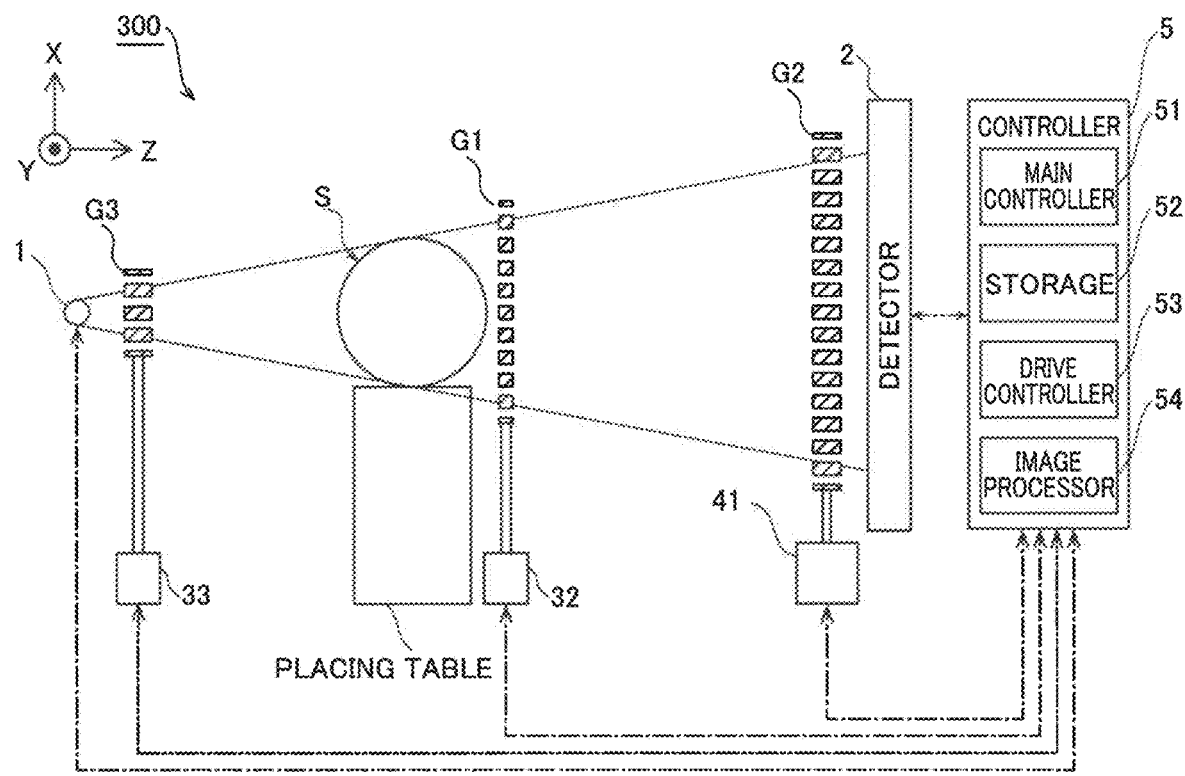
FIG. 14 is a diagram showing the overall structure of an X-ray phase imaging apparatus in which each grating is movable according to a modified example of the embodiment of the present invention.

While the example in which the adjustment mechanism 3 on which the subject S is placed is moved such that the subject S is moved relative to the imaging grating G1 has been shown in the aforementioned embodiment, the present invention is not restricted to this. According to the present invention, a structure other than the subject S may be moved. Specifically, as shown in FIG. 14, an X-ray phase imaging apparatus 300 may further include an adjustment mechanism 32 that moves the imaging grating G1, an adjustment mechanism 33 that moves the light source grating G3, and a movement mechanism 41 that moves the absorption grating G2, for example. In this case, the controller 5 moves the imaging grating G1 with the adjustment mechanism 32, the adjustment mechanism 33, and the movement mechanism 41 so as to change the relative position between the subject S and the imaging grating G1. At this time, the controller 5 moves the imaging grating G1, the absorption grating G2, and the light source grating G3 while maintaining the relative positions of the absorption grating G2 and the light source grating G3 to the imaging grating G1. Note that the movement by the movement mechanism 41 also serves as the movement of the absorption grating G2 for obtaining the step curves and the movement of the relative position of the absorption grating G2 to the subject S. Furthermore, in this case, there is no adjustment mechanism 3, and the subject S is placed on a placing table including no adjustment mechanism. Therefore, the position of the subject S remains fixed.

Figure 15:
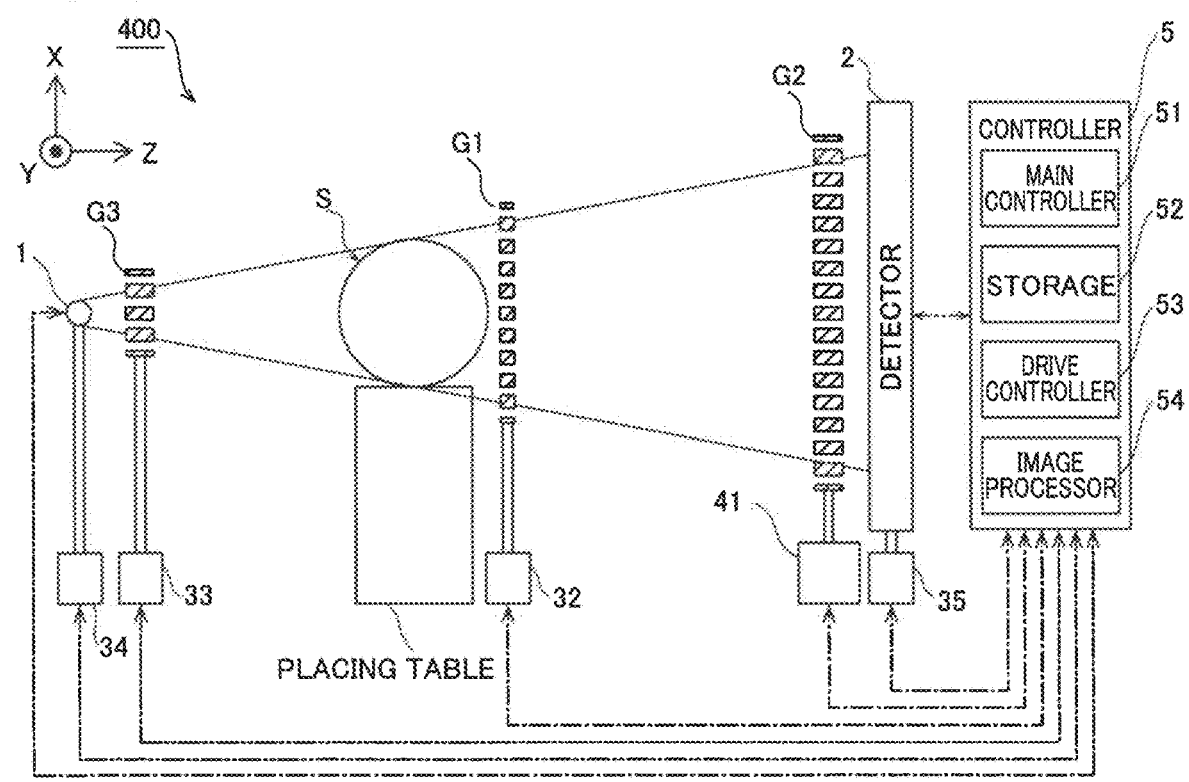
FIG. 15 is a diagram showing the overall structure of an X-ray phase imaging apparatus in which an X-ray source, a detector, and each grating are movable according to a modified example of the embodiment of the present invention.

Furthermore, as shown in FIG. 15, an X-ray phase imaging apparatus 400 may further include an adjustment mechanism 34 that moves the X-ray source 1 and an adjustment mechanism 35 that moves the detector 2 in addition to the above adjustment mechanisms 32 and 33 and the above movement mechanism 41, for example. At this time, the imaging grating G1, the X-ray source 1, the detector 2, the light source grating G3, and the absorption grating G2 are moved while the relative positions of the X-ray source 1, the detector 2, the absorption grating G2, and the light source grating G3 to the imaging grating G1 are maintained. In this case, the controller 5 changes the relative position between the subject S and the imaging grating G1 by moving the entire X-ray phase imaging apparatus 400 with respect to the subject S, for example.

Figure 16:
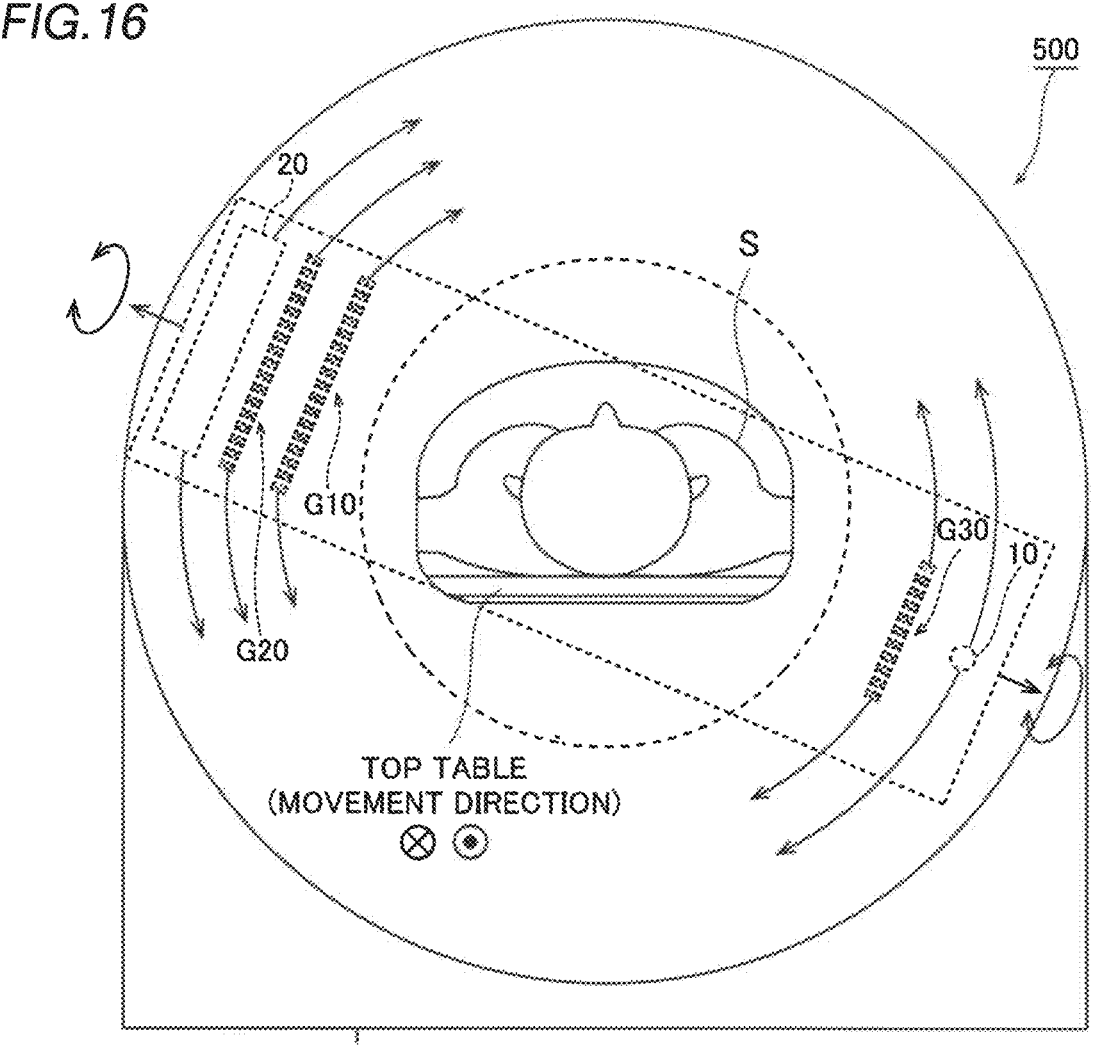
FIG. 16 is a diagram showing the overall structure of an X-ray phase imaging apparatus in which an X-ray source, a detector, each grating, and a subject are movable according to a modified example of the embodiment of the present invention.

Furthermore, as shown in FIG. 16, an X-ray phase imaging apparatus 500 may move the X-ray source 10, the detector 20, an absorption grating G20, a light source grating G30, and an imaging grating G10 while maintaining the relative positions of the X-ray source 10, the detector 20, the absorption grating G20, and the light source grating G30 to the imaging grating G1 so as to move the subject S, for example. In this case, the subject S is a human body lying on a top table, for example, and moves with movement of the top table. For example, the imaging grating G10 etc. can move in the directions of the arrows, and the top table can move in a forward-rearward direction (rear side and front side) with respect to the plane of the figure.

Figure 17:
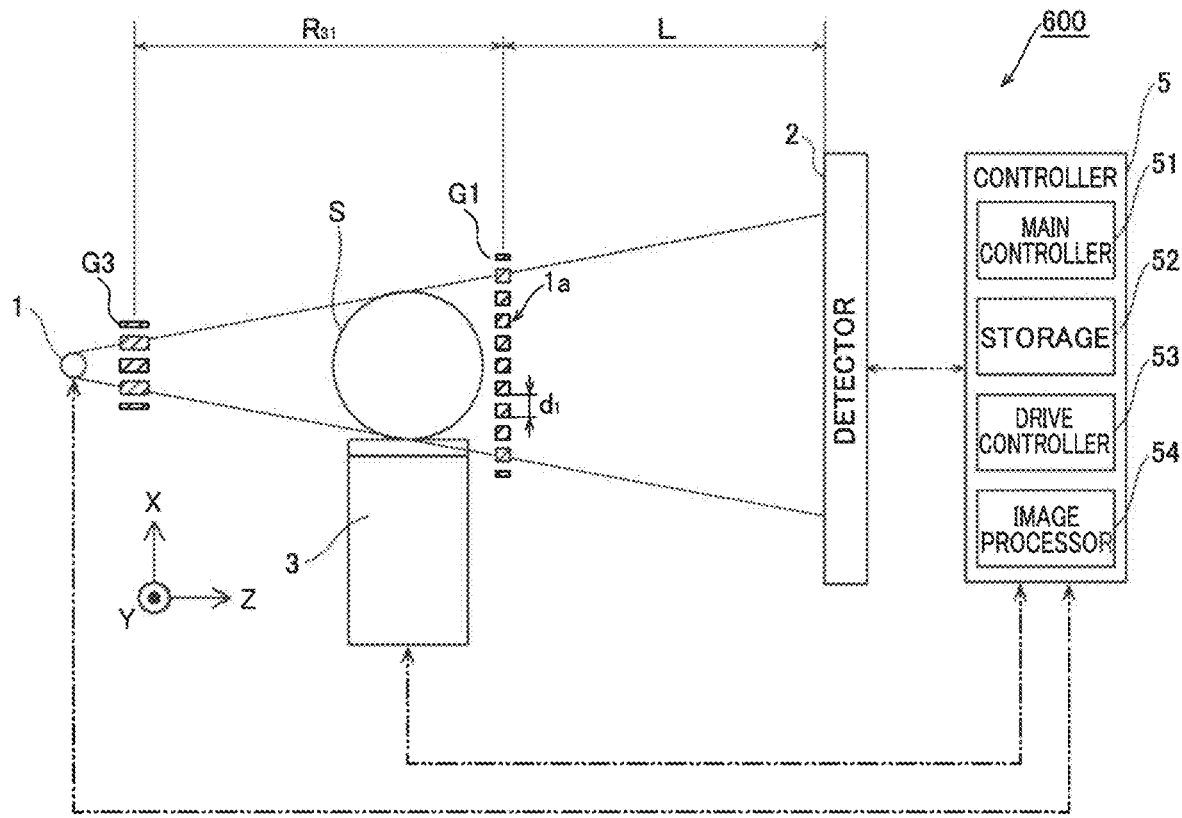
FIG. 17 is a diagram showing the overall structure of an X-ray phase imaging apparatus in which the arrangement of an absorption grating is omitted according to a modified example of the embodiment of the present invention.

While the example in which the absorption grating G2 is disposed has been shown in the aforementioned embodiment, the present invention is not restricted to this. According to the present invention, the absorption grating G2 may not be disposed. In this case, it is preferable to dispose the detection surface of the detector 2 at a position at which the self-image G0 by the imaging grating appears. Specifically, it becomes like an X-ray phase imaging apparatus 600 shown in FIG. 17. Here, a distance L between the detection surface of the detector 2 and the imaging grating G1 is equal to $z_p$ in the formula (1). At this time, the detector 2 directly detects the self-image (grating image) G0 generated by the imaging grating G1, and thus a highly sensitive detector having a high resolution (the size of each pixel is small) is preferable. Note that the grating image detected by the detector 2 may not be the self-image G0.

Figure 18:
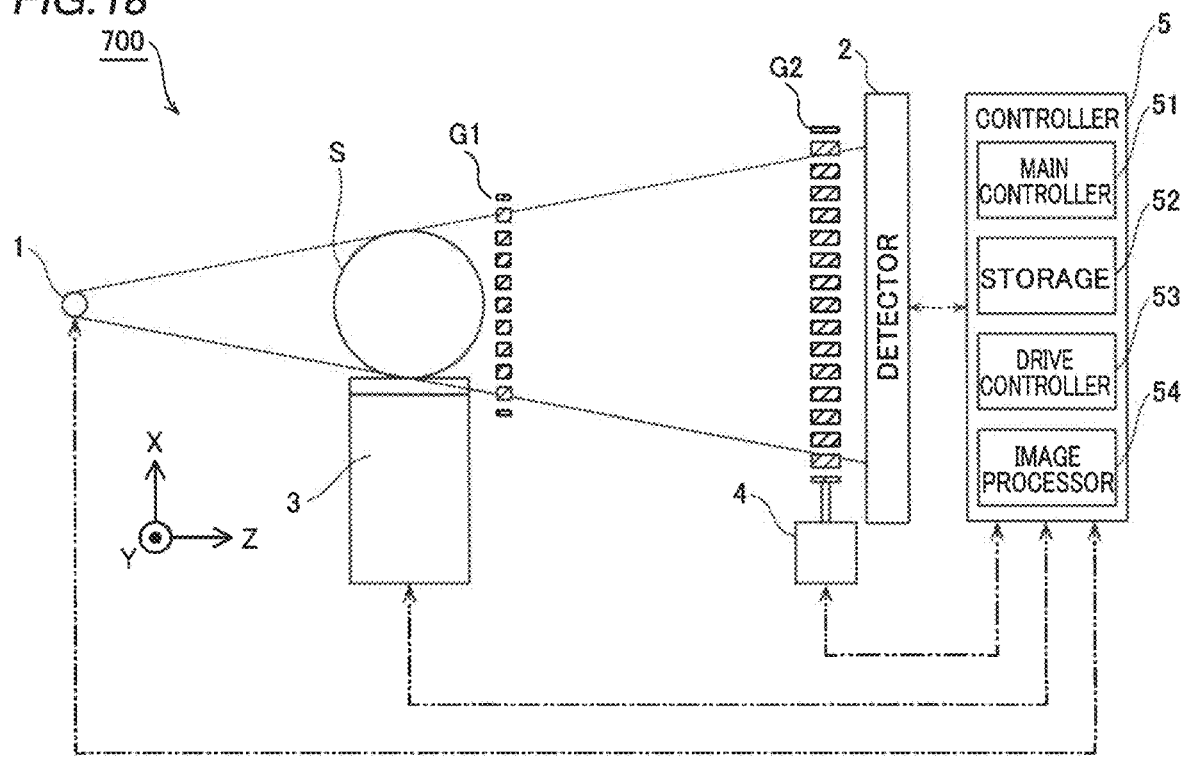
FIG. 18 is a diagram showing the overall structure of an X-ray phase imaging apparatus in which the arrangement of a light source grating is omitted according to a modified example of the embodiment of the present invention.

While the example in which the light source grating G3 is disposed has been shown in the aforementioned embodiment, the present invention is not restricted to this. According to the present invention, the light source grating G3 may not be disposed. Specifically, it becomes like an X-ray phase imaging apparatus 700 shown in FIG. 18. In this case, it is necessary to align the phases of the X-rays radiated from the X-ray source 1. Therefore, the X-ray source 1 includes a synchrotron radiation facility (accelerator facility) or a micro focus X-ray source, for example. The light source grating G3 may be replaced by a single slit (one-dimensional or dotted single slit) (not shown).

Figure 19:
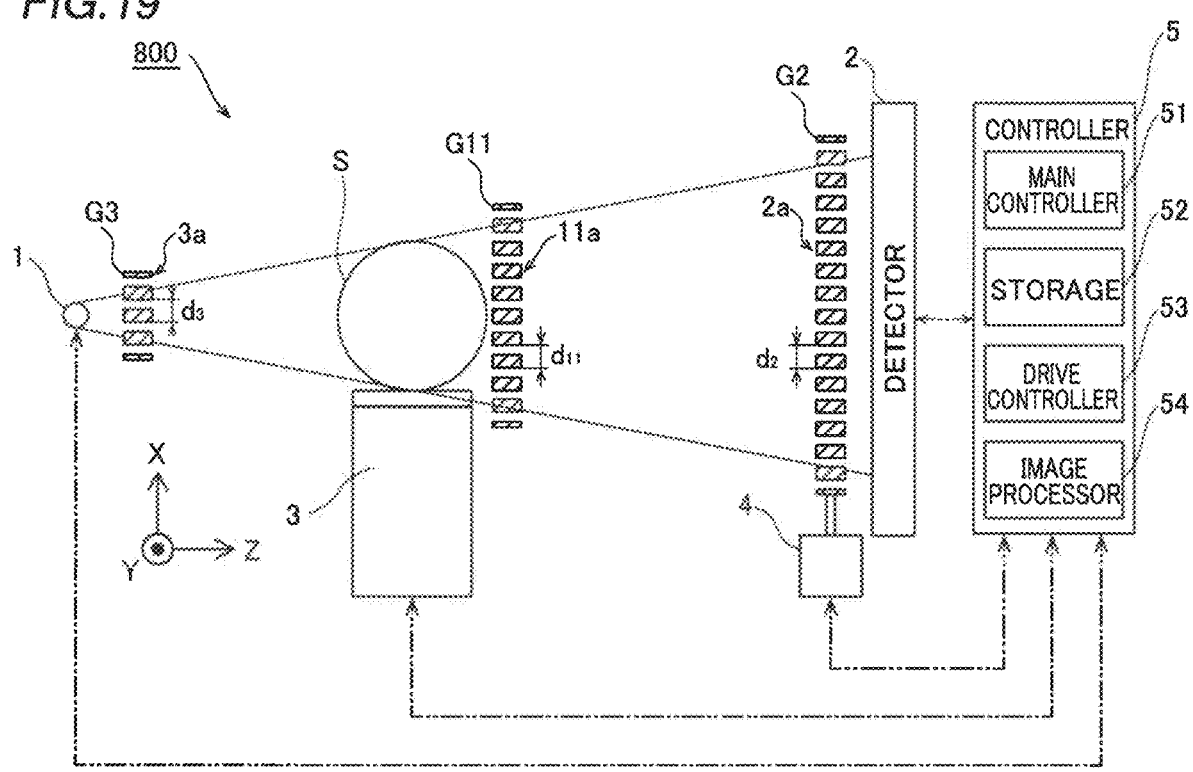
FIG. 19 is a diagram showing the overall structure of an X-ray phase imaging apparatus in which an imaging grating includes an absorption type grating according to a modified example of the embodiment of the present invention.

While the example in which the imaging grating G1 includes a phase type diffraction grating in which the X-rays that have passed therethrough cause interference due to diffraction has been shown in the aforementioned embodiment, the present invention is not restricted to this. According to the present invention, an imaging grating G11 including an absorption type grating may be disposed. Specifically, it becomes like an X-ray phase imaging apparatus 800 shown in FIG. 19. In this case, the period (pitch) $d_{11}$ of the imaging grating G11 is relatively large enough not to cause interference by the X-rays. Thus, interference fringes are not generated due to the X-rays that have passed through the imaging grating G11 (have been diffracted). Consequently, a grating image generated by the imaging grating G11 has a light and dark striped pattern not due to interference that reflects X-ray absorption by absorption members 11a and transparent portions of the imaging grating G11. In this case, there is no constraint such as the self-image G0 at the position at which the grating image is acquired, and thus it is possible to dispose the gratings relatively freely. In addition, the period (pitch) of the imaging grating G11 is large such that the periods (pitches) of the absorption grating G2 and the light source grating G3 can also be large. Thus, it is easy to manufacture the gratings. In addition, it is easy to make the opening area of the imaging grating G11 including an absorption type diffraction grating larger than that of the imaging grating G1 including a phase type diffraction grating. Thus, it is possible to acquire a relatively large X-ray image I in imaging corresponding to one position.

Note that the change of the arrangement of the subject S, the change of the subject to be relatively moved (at least one of the subject S and the structure of the apparatus), the omission of the absorption grating G2, the omission of the light source grating G3, and the change of the type of imaging grating G1 may be combined with each other. In the X-ray phase imaging apparatuses 200, 300, 400, 500, 600, 700, and 800 according to the above modified examples, description of the same structures and effects as those of the above embodiment is omitted.

While the X-ray image acquisition processing and the dark field image contrast adjustment processing performed by the controller 5 have been illustrated using flowcharts in a "flow-driven manner" for the convenience of illustration in the aforementioned embodiment, the present invention is not restricted to this. According to the present invention, the processing performed by the controller 5 may be performed in an "event-driven manner" in which processing is performed on an event basis. In this case, the processing may be performed in a complete event-driven manner or in a combination of an event-driven manner and a flow-driven manner.

DESCRIPTION OF REFERENCE NUMERALS 1, 10: X-ray source
2, 20: detector
3, 31, 32, 33, 34, 35: adjustment mechanism
4, 41: movement mechanism
5: controller
100, 200, 300, 400, 500, 600, 700, 800: X-ray phase imaging apparatus
G1, G10, G11: imaging grating
G2, G20: absorption grating
G3, G30: light source grating
Ia: absorption image
Id: phase differential image
Iv: dark field image
ROI: region of interest
S: subject
Sa: fruit
Sb: fiber material

The invention claimed is:

1. An X-ray phase imaging apparatus comprising:
an X-ray source that radiates X-rays to a subject;
an imaging grating that generates a grating image by transmitting the X-rays radiated to the subject from the X-ray source;
a detector that detects the X-rays that have been transmitted through the imaging grating;
an adjustment mechanism that changes and adjusts a relative position between the subject and the imaging grating; and
a controller that generates a dark field image representing a change in X-ray sharpness between a case in which the subject is present and a case in which the subject is not present based on signals of the X-rays detected by the detector with respect to each of a plurality of relative positions between the subject and the imaging grating changed by the adjustment mechanism to acquire a contrast of a region of interest in the dark field image, and controls the adjustment mechanism to adjust the relative position between the subject and the imaging grating based on the acquired contrast.

2. The X-ray phase imaging apparatus according to claim 1, wherein the controller controls the adjustment mechanism to adjust the relative position between the subject and the imaging grating so as to correspond to the dark field image in which the contrast of the region of interest is relatively high.

3. The X-ray phase imaging apparatus according to claim 1, wherein the controller causes a position of the region of interest to follow a change in the relative position between the subject and the imaging grating based on the contrast when changing the relative position between the subject and the imaging grating based on the acquired contrast.

4. The X-ray phase imaging apparatus according to claim 1, wherein the controller acquires the dark field image and information about the relative position between the subject and the imaging grating with respect to each of the plurality of relative positions between the subject and the imaging grating, and stores the dark field image and the information about the relative position in association with each other.

5. The X-ray phase imaging apparatus according to claim 1, wherein the controller moves at least one of the subject and the imaging grating from the relative position between the subject and the imaging grating at which the contrast of the region of interest of the dark field image is determined to be maximum among a plurality of dark field images obtained in a first direction to the plurality of relative positions between the subject and the imaging grating in a second direction different from the first direction, and increases the contrast of the dark field image.

6. The X-ray phase imaging apparatus according to claim 1, wherein the controller acquires the contrast of the dark field image based on an absolute value of a difference between an average value of pixel values in the region of interest and an average value of pixel values in a background region.

7. The X-ray phase imaging apparatus according to claim 1, further comprising at least one of an absorption grating disposed between the X-ray source and the detector, disposed behind the subject and the imaging grating as viewed from the X-ray source, and that detects the grating image generated by the imaging grating, and a light source grating disposed between the X-ray source and the detector, disposed in front of the subject and the imaging grating as viewed from the X-ray source, and that aligns phases of the X-rays such that the X-rays that have passed therethrough interfere with each other, wherein
when adjusting the relative position between the subject and the imaging grating, the adjustment mechanism maintains a relative position between at least one of the absorption grating and the light source grating and the imaging grating.

8. The X-ray phase imaging apparatus according to claim 1, wherein the adjustment mechanism adjusts the relative position between the subject and the imaging grating while maintaining relative positions of the X-ray source and the detector to the imaging grating.

9. The X-ray phase imaging apparatus according to claim 1, wherein the controller further acquires an absorption image representing a degree of X-ray absorption by the subject and a phase differential image representing a change in X-ray phase due to the subject.

* * * * *